United States Patent
Nakazato et al.

(10) Patent No.: US 6,949,552 B2
(45) Date of Patent: Sep. 27, 2005

(54) REMEDIAL AGENT FOR ANXIETY NEUROSIS OR DEPRESSION AND PIPERAZINE DERIVATIVE

(75) Inventors: Atsuro Nakazato, Satte (JP); Shigeyuki Chaki, Saitama (JP); Taketoshi Okubo, Asaka (JP); Shin-ichi Ogawa, Okegawa (JP); Takaaki Ishii, Saitama (JP)

(73) Assignee: Taisho Pharmaceutical Co., Ltd. (JP)

( * ) Notice: Subject to any disclaimer, the term of this patent is extended or adjusted under 35 U.S.C. 154(b) by 247 days.

(21) Appl. No.: 10/311,429

(22) PCT Filed: Jun. 27, 2001

(86) PCT No.: PCT/JP01/05524

§ 371 (c)(1),
(2), (4) Date: Dec. 18, 2002

(87) PCT Pub. No.: WO02/00259

PCT Pub. Date: Jan. 3, 2002

(65) Prior Publication Data

US 2003/0186992 A1 Oct. 2, 2003

(30) Foreign Application Priority Data

Jun. 27, 2000 (JP) ........................................ 2000-192856

(51) Int. Cl.$^7$ .................... A61K 31/496; C07D 401/06; C07D 403/06; C07D 413/14
(52) U.S. Cl. .............................. 514/252.11; 514/252.18; 514/253.01; 514/253.06; 514/253.12; 544/295; 544/357; 544/360; 544/363; 544/364
(58) Field of Search ................................ 544/357, 360, 544/364, 295, 363; 514/253.12, 252.11, 253.01

(56) References Cited

U.S. PATENT DOCUMENTS

| 5,177,078 A | 1/1993 | Ward et al. ................. 514/253 |
| 5,532,242 A | 7/1996 | Cliffe ......................... 514/255 |

FOREIGN PATENT DOCUMENTS

| DE | 20 38 206 A | 2/1971 | |
| EP | 0 262 993 | 4/1988 | |
| EP | 0479546 A2 | 4/1992 | ......... C07D/403/06 |
| FR | 1317053 | 2/1963 | |
| JP | 6-41071 | 2/1994 | ......... C07D/209/14 |
| WO | WO 93/14076 | 7/1993 | ......... C07D/295/12 |
| WO | WO 98/37097 | 8/1998 | ........... C07K/14/68 |
| WO | 99 64002 A | 12/1999 | |
| WO | PCT/JP01/05524 | 6/2001 | |

OTHER PUBLICATIONS

Vedjelek Z. et al., "Potential antitussives: synthesis and pharmacology of a series of 1-[2-amino-2(4-fluorophenyl)ethyl]-4-(2-benzoylpropyl) piperazines", Collect. Czech. Chem. Commun., (1983), vol. 48, No. 10, pp. 2977 to 2988.

Kask A. et al., "Discovery of a novel superpotent and selective melanocortin-4 receptor antagonist (HS024): evaluation in vitro and in vivo", Endocrinology, (1998), vol. 139, No. 12, pp. 5006 to 5014.

*Primary Examiner*—Emily Bernhardt
(74) *Attorney, Agent, or Firm*—Lorusso & Loud

(57) ABSTRACT

There are provided a therapeutic preparation for anxiety neurosis or depression which comprises a $MC_4$ receptor antagonist as an effective ingredient; and a piperazine derivative represented by Formula [1]:

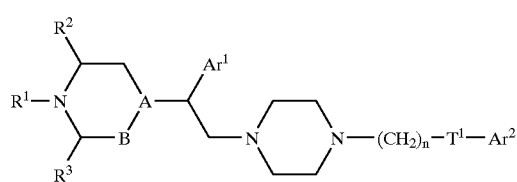

[wherein Ar¹ is a phenyl group, a substituted phenyl group, a naphthyl group or a substituted naphthyl group; Ar² is a naphthyl group, a substituted naphthyl group, a quinolyl group, a group represented by the formula:

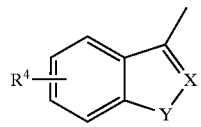

(wherein $R^4$ is a hydrogen atom or a halogen atom; and X—Y is CH—NH, CH—O, CH—S or N—O) or a group represented by the formula:

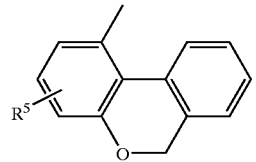

(wherein $R^5$ is a hydrogen atom, a hydroxyl group or a $C_{1-10}$ alkoxy group); $R^1$ is a hydrogen atom, a $C_{1-10}$ alkyl group, a $C_{3-8}$ cycloalkyl group, a $C_{3-10}$ alkenyl group, a phenyl group, a 1-cyanoethyl group, a pyrimidin-2-yl group or an amidyl group; $R^2$ and $R^3$ are the same or different, and are each a hydrogen atom or a $C_{1-10}$ alkyl group; A-B is N—$CH_2$, CH—$CH_2$, C(OH)—$CH_2$ or C=CH; $T^1$ is a single bond, —N($R^6$)— (wherein $R^6$ is a hydrogen atom or a $C_{1-10}$ alkyl group), —O—, —CH=CH— or —C(=O)—; n is an integer of from 1 to 10 and when $T^1$ is a single bond, —CH=CH— or —C(=O)—, n is an integer of from 2 to 10 when $T^1$ is —N($R^6$)— or —O—], or a pharmaceutically acceptable salt thereof.

12 Claims, 2 Drawing Sheets

N = 7~12    #: p<0.05; # #: p<0.01 vs vehicle

N = 10    **: p<0.01 vs control
#: p<0.01 vs vehicle

REMEDIAL AGENT FOR ANXIETY NEUROSIS OR DEPRESSION AND PIPERAZINE DERIVATIVE

BACKGROUND ART

The present invention relates to a therapeutic preparation for anxiety neurosis or depression which comprises a $MC_4$ receptor antagonist as an effective ingredient, and relates to novel piperazine derivatives having a $MC_4$ receptor antagonistic action.

It is suggested by the recent progress of pathophysiology that stress is deeply pertinent to development mechanism of anxiety neurosis and depression. As an intracerebral reaction caused by stress, there has been known a functional abnormality of neuroendocrine system of which representative is the functional abnormality of hypothalamus-pituitary-adrenal system. From such a background, the neuropeptides which locate in pituitary and affect neuroendocrine attract attention as a development reason of depression/anxiety.

Among such neuropeptides are corticotropin releasing factors (CRF) and proopiomelanocortin (POMC). CRF is known to play the central role of stress reaction such as susceptibility of hypothalamus-pituitary-adrenal system, and suggested to have relation to anxiety/depression. Melanocortins [adrenocorticotropic hormone (ACTH), melanocyte stimulating hormone (MSH)] produced from POMC are main neuropeptides in hypothalamus, but there is no report of the substances acting to melanocortin receptors relating to stress reaction and depression/anxiety neurosis.

Melanocortin receptors are classified into 5 subtypes of $MC_1$–$MC_5$. Among these subtypes, melanocortin receptor subtype $MC_4$ is reported as peptidergic selective agonist or antagonist, but there is no report on stress reaction and anti-anxiety action of these agonists or antagonists. Compound 4 of the present invention in Table 1 acts as a high selective antagonist in recombinant human melanocortin receptors.

The relation of melanocortin receptor subtypes and anxiety/depression and stress reaction, and novel piperazine derivatives have been investigated.

DISCLOSURE OF THE INVENTION

As a result of extensive research of the above-mentioned subject, $MC_4$ receptor agonists have been found to have anxiety inducing action, and $MC_4$ receptor antagonists have been found to be effective for treatment of anxiety neurosis and depression because of their anti-stress, anti-anxiety and anti-depression actions. Furthermore, novel piperazine derivatives of $MC_4$ receptor antagonists have been found, and thereby the present invention has been accomplished.

The present invention is described as follows:

The present invention contains the following three items.

1. A therapeutic preparation for anxiety neurosis or depression which comprises a $MC_4$ receptor antagonist as an effective ingredient.

2. The therapeutic preparation for anxiety neurosis or depression wherein the $MC_4$ receptor antagonist is a piperazine derivative represented by Formula [1]:

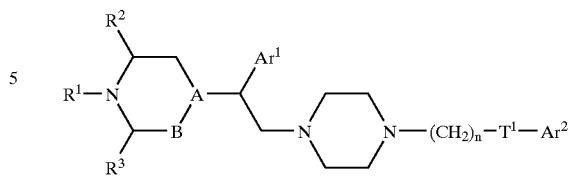

[wherein $Ar^1$ is a phenyl group, a substituted phenyl group, a naphthyl group or a substituted naphthyl group; $Ar^2$ is a naphthyl group, a substituted naphthyl group, a quinolyl group, a group represented by the formula:

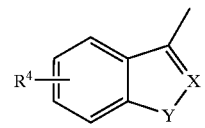

(wherein $R^4$ is a hydrogen atom or a halogen atom, and X—Y is CH—NH, CH—O, CH—S or N—O) or a group represented by the formula:

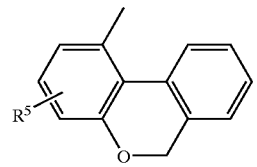

(wherein $R^5$ is a hydrogen atom, a hydroxyl group or a $C_{1-10}$ alkoxy group); $R^1$ is a hydrogen atom, a $C_{1-10}$ alkyl group, a $C_{3-8}$ cycloalkyl group, a $C_{3-10}$ alkenyl group, a phenyl group, a 1-cyanoethyl group, a pyrimidin-2-yl group or an amidyl group; $R^2$ and $R^3$ are the same or different, and are each a hydrogen atom or a $C_{1-10}$ alkyl group; A-B is N—$CH_2$, CH—$CH_2$, C(OH)—$CH_2$ or C=CH; $T^1$ is a single bond, —N($R^6$)— (wherein $R^6$ is a hydrogen atom or a $C_{1-10}$ alkyl group), —O—, —CH=CH— or —C(=O)—; n is an integer of from 1 to 10 when $T^1$ is a single bond, —CH=CH— or —C(=O)—, and n is an integer of from 2 to 10 when $T^1$ is —N($R^6$)— or —O—], or a pharmaceutically acceptable salt thereof.

3. The piperazine derivative represented by the above-mentioned Formula [1] or a pharmaceutically acceptable salt thereof.

In the present invention, the antagonist which belongs to $MC_4$ receptor means a compound which has an antagonistic action to $MC_4$ receptor, and preferably means a compound having an concentration-dependent inhibition action in the receptor binding test using $MC_4$ receptor-expressed cells according to the method described in J. Biol. Chem., 268; 15174–15179, 1993, having equivalent or higher affinity to $MC_4$ receptor than α-MSH, and antagonizing to an action of α-MSH when the amount of cAMP stimulated by α-MSH is measured by means of a cAMP measurement kit.

The terms used in the present invention are defined as follows. In the present invention, "$C_{x-y}$" means that the group referred thereto contains the number of carbon atoms which ranges from x to y.

The substituted phenyl group refers to a phenyl group substituted with 1 to 3 substituents selected arbitrarily from the group consisting of a $C_{1-10}$ alkyl group, a $C_{3-8}$ cycloalkyl group, a $C_{3-8}$ cycloalkyl $C_{1-5}$ alkyl group, a $C_{1-10}$ alkoxy group, a $C_{3-8}$ cycloalkoxy group, a $C_{3-8}$ cycloalkyl $C_{1-5}$ alkoxy group, a benzyloxy group, a hydroxyl group, a halogen atom, a nitro group, a group of the formula: $NR^{11}(R^{22})$(wherein $R^{11}$ and $R^{22}$ are the same or different, and are each a hydrogen atom or a $C_{1-6}$ alkyl group, or $R^{11}$ and $R^{22}$ together with the nitrogen atom to which they are attached form a 5–8 membered cyclic amine), a trifluoromethyl group, a cyano group, a carbamoyl group and a phenyl group, and preferably a phenyl group substituted with 1 to 3 substituents selected arbitrarily from the group consisting of a $C_{1-10}$ alkyl group, a $C_{1-10}$ alkoxy group, a benzyloxy group, a hydroxyl group, a halogen atom, a nitro group, an amino group, an amino group substituted with one or two $C_{1-6}$ alkyl groups, a trifluoromethyl group, a cyano group, a carbamoyl group and a phenyl group; and examples of which are a 2-methylphenyl group, a 3-methylphenyl group, a 4-methylphenyl group, a 2-ethylphenyl group, a 3-ethylphenyl group, a 4-ethylphenyl group, a 2-propylphenyl group, a 3-propylphenyl group, a 4-propylphenyl group, a 2-cyclopentylphenyl group, a 2-methoxyphenyl group, a 3-methoxyphenyl group, a 4-methoxyphenyl group, a 4-ethoxyphenyl group, a 4-isopropoxyphenyl group, a 4-benzyloxyphenyl group, a 4-hydroxyphenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 4-nitrophenyl group, a 4-aminophenyl group, a 4-trifluoromethylphenyl group, a 3-cyanophenyl group, a 4-cyanophenyl group, a 3-carbamoylphenyl group, a 4-carbamonylphenyl group and a 4-biphenyl group.

The substituted naphthyl group refers to a naphthyl group substituted with 1 to 3 substituents selected arbitrarily from the group consisting of a $C_{1-10}$ alkyl group, a $C_{3-8}$ cycloalkyl group, a $C_{3-8}$ cycloalkyl $C_{1-5}$ alkyl group, a $C_{1-10}$ alkoxy group, a $C_{3-8}$ cycloalkoxy group, a $C_{3-8}$ cycloalkyl $C_{1-5}$ alkoxy group, a benzyloxy group, a hydroxyl group, a $C_{1-5}$ alkoxycarbonylmethoxy group, a carbamoylmethoxy group, a halogen atom, a nitro group, a group of the formula: $NR^{33}(R^{44})$(wherein $R^{33}$ and $R^{44}$ are the same or different, and are each a hydrogen atom or a $C_{1-6}$ alkyl group, or $R^{33}$ and $R^{44}$, together with the nitrogen atom to which they are attached, form a 5–8 membered cyclic amine) and a trifluoromethyl group; and preferably a naphthyl group substituted with 1 to 3 substituents selected arbitrarily from the group consisting of a $C_{1-10}$ alkyl group, a $C_{1-10}$ alkoxy group, a hydroxyl group, a $C_{1-5}$ alkoxycarbonylmethoxy group, a carbamoylmethoxy group, a halogen atom, an amino group, and an amino group substituted with one or two $C_{1-6}$ alkyl groups; and examples of which are a 2-methylnaphthalen-1-yl group, a 3-methylnaphthalen-1-yl group, a 4-methylnaphthalen-1-yl group, a 2-ethylnaphthalen-1-yl group, a 3-ethylnaphthalen-1-yl group, a 4-ethylnaphthalen-1-yl group, a 2-propylnaphthalen-1-yl group, a 3-propylnaphthalen-1-yl group, a 4-propylnaphthalen-1-yl group, a 2-methoxynaphthalen-1-yl group, a 3-methoxynaphthalen-1-yl group, a 4-methoxynaphthalen-1-yl group, a 6-methoxynaphthalen-1-yl group, a 4-ethoxynaphthalen-1-yl group, a 4-isopropoxynaphthalen-1-yl group, a 4-benzyloxynaphthalen-1-yl group, a 2-hydroxynaphthalen-1-yl group, a 4-hydroxynaphthalen-1-yl group, a 2-methoxycaronylmethoxynaphthalen-1-yl group, a 2-carbamoylmethoxynaphthalen-1-yl group, a 2-fluoronaphthalen-1-yl group, a 3-fluoronaphthalen-1-yl group, a 4-fluoronaphthalen-1-yl group, a 2-chloronaphthalen-1-yl group, a 3-chloronaphthalen-1-yl group, a 4-chloronaphthalen-1-yl group, a 2-bromonaphthalen-1-yl group, a 3-bromonaphthalen-1-yl group, a 4-bromonaphthalen-1-yl group, a 4-nitronaphthalen-1-yl group, a 4-aminonaphthalen-1-yl group, a 4-trifluoromethylnaphthalen-1-yl group and a 4-dimethylaminonaphthalen-1-yl group.

The $C_{1-10}$ alkyl group refers to a straight or branched alkyl group having 1 to 10 carbon atoms, and examples which are a methyl group, an ethyl group, a propyl group, an isopropyl group, a butyl group, an isobutyl group, a pentyl group, an isopentyl group, a 1-ethylpropyl group, a hexyl group, an isohexyl group, a 1-ethylbutyl group, a heptyl group, an isoheptyl group, an octyl group, a nonyl group and a decyl group. The $C_{3-8}$ cycloalkyl group refers to a cycloalkyl group having 3 to 8 carbon atoms, and examples of which are a cyclopropyl group, a cyclobutyl group, a cyclopentyl group and a cyclohexyl group. The $C_{3-8}$ cycloalkyl $C_{1-5}$ alkyl group refers to a $C_{1-5}$ alkyl group substituted with a cycloalkyl group having 3 to 8 carbon atoms, and examples of which are a cyclopropylmethyl group, a cyclobutylmethyl group, a cyhclopentylmethyl group and a cyclohexylmethyl group.

The $C_{3-10}$ alkenyl group refers to a straight or branched alkenyl group having 3 to 10 carbon atoms, and examples of which are an allyl group, a 1-buten-4-yl group, a 2-buten-4-yl group, a 1-penten-5-yl group, a 2-penten-5-yl group and a prenyl group.

The $C_{1-10}$ alkoxy group refers to a straight or branced alkoxy group having 1 to 10 carbon atoms; and examples of which are a methoxy group, an ethoxy group, a propoxy group, an isopropoxy group, a butoxy group, an isobutoxy group, a pentyloxy group, an isopentyloxy group, a hexyloxy group, a heptyloxy group, an octyloxy group, a nonyloxy group and a decyloxy group. The $C_{3-8}$ cycloalkoxy group refers to a cycloalkoxy group having 3 to 8 carbon atoms; and examples of which are a cyclopropoxy group, a cyclopentyloxy group and a cyclooctyloxy group. The $C_{3-8}$ cycloalkyl $C_{1-5}$ alkoxy group refers to the $C_{1-5}$ alkoxy group substituted with a cycloalkyl group having 3 to 8 carbon atoms; and examples of which are a cyclopropylmethoxy group, a cyclopentylmethoxy group and a cyclohexylethoxy group.

The amino group substituted with one or two $C_{1-6}$ alkyl groups refers to an amino group substituted with 1 or 2 members of a straight or branched alkyl groups having 1 to 6 carbon atoms; and examples of which are a methylamino group, an ethylamino group, a propylamino group, a dimethylamino group, diethylamino group and a dipropylamino group.

Examples of the amino group represented by the formula: $NR^{11}(R^{22})$ are a methylamino group, an ethylamino group, a propylamino group, a dimethylamino group, a diethylamino group and a dipropylamino group. Furthermore, examples of the cyclic amino group represented by the formula: $NR^{11}(R^{22})$ are a pyrrolidino group, a piperidino group, a piperazino group, a morpholino group and a thiomorpholino group.

Examples of the amino group represented by the formula: $NR^{33}(R^{44})$ are a methylamino group, an ethylamino group, a propylamino group, a dimethylamino group, a diethylamino group and a dipropylamino group. Furthermore, examples of the cyclic amino group represented by the formula: $NR^{33}(R^{44})$ are a pyrrolidino group, a piperidino group, a piperazino group, a morpholino group and a thiomorpholino group.

The halogen atom refers to a fluorine atom, a chlorine atom, a bromine atom or an iodine atom.

Examples of the pharmaceutically acceptable salt in the present invention are salts with mineral acids such as sulfuric acid, hydrochloric acid or phosphoric acid, or salts with organic acids such as acetic acid, oxalic acid, lactic acid, tartaric acid, fumaric acid, maleic acid, methanesulfonic acid or benzenesulfonic acid.

The compounds of Formula [1] can be prepared by the following General Preparation Methods 1 to 17 (in the following reaction schemes, $Ar^1$, $Ar^2$, $R^6$, $T^1$ and n are defined above; $X^1$ is a chlorine atom, a bromine atom or an iodine atom; $A^1$-$B^1$ is CH—$CH_2$, C(OH)—$CH_2$ or C=CH; $T^2$ is a single bond, —$N(R^6)$— or —O—; $R^7$ is a $C_{1-10}$ alkyl group; $R^8$ is a $C_{1-10}$ alkyl group, a $C_{3-10}$ alkenyl group, a phenyl group or a pyrimidin-2-yl group; and $R^9$ is an ordinary amino-protective group such as a t-butoxycarbonyl group, an ethoxycarbonyl group or a benzyloxycarbonyl group; $R^{10}$ is a $C_{1-10}$ alkyl group, a 1-cyanoethyl group or an amidino group; $R^{11}$ is the group defined for $R^9$ other than a t-butoxycarbonyl group; Boc group is a t-butoxycarbonyl group; Bn group is a benzyl group and * means optically active).

[General preparation method 1]

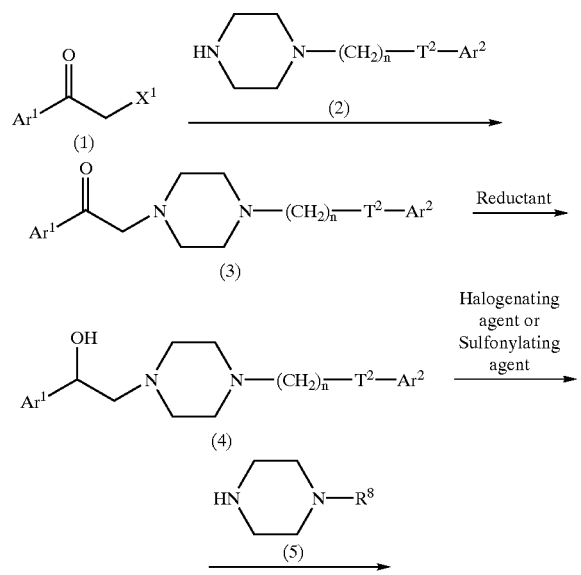

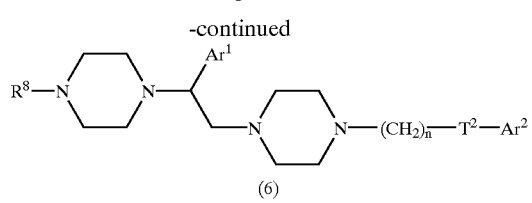

A compound (1) can be reacted with a compound (2) in the presence or absence of a base in an inert solvent to convert to a compound (3), followed by reduction of the carbonyl group in an inert solvent to synthesize a compound (4). The compound (4) can be reacted with a halogenating agent or a sulfonylating agent such as an alkylsulfonyl halide or an arylsulfonyl halide in the presence or absence of a base in an inert solvent, thereby the hydroxyl group is converted to a suitable leaving group. Then, a compound (5) can be reacted in the presence or absence of a base in an inert solvent to give a compound (6) of the present invention.

The base includes, for example, organic amines (e.g., triethylamine, diisopropylethylamine and pyridine) and inorganic bases (e.g., potassium carbonate, sodium bicarbonate, sodium hydroxide, potassium hydroxide and sodium hydride). The reduction includes, for example, a reduction under an acidic, neutral or basic condition using a boron reductant (e.g. sodium borohydride, sodium cyanoborohydride, lithium borohydride, L-Selectride and K-Selectride) or an aluminum reductant (e.g. lithium aluminum hydride, Red-Al or diisobutyl aluminum hydride). The halogenating agent includes an ordinary halogenating agent of the hydroxyl group (e.g., thionyl chloride, thionyl bromide or phosphoryl chloride). The sulfonylating agent such as an alkylsulfonyl halide or an arylsulfonyl halide include, for example, ordinary sulfonylating agents of the alcohol (e.g. methanesulfonyl chloride, benzenesulfonyl chloride, toluenesulfonyl chloride or trifluoromethanesulfonyl chloride). The inert solvent include, for example, alcohols (e.g., methanol and ethanol), ethers (e.g., diethyl ether and tetrahydrofuran), hydrocarbons (e.g., toluene and benzene), halogenated carbon type solvents (e.g., chloroform and dichloromethane), dimethylformamide, acetonitrile, water and a mixture thereof.

[General preparation method 2]

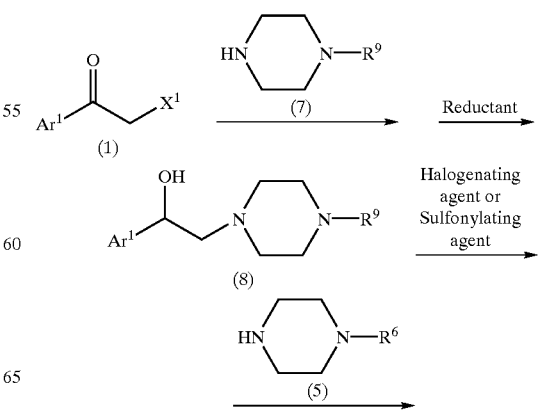

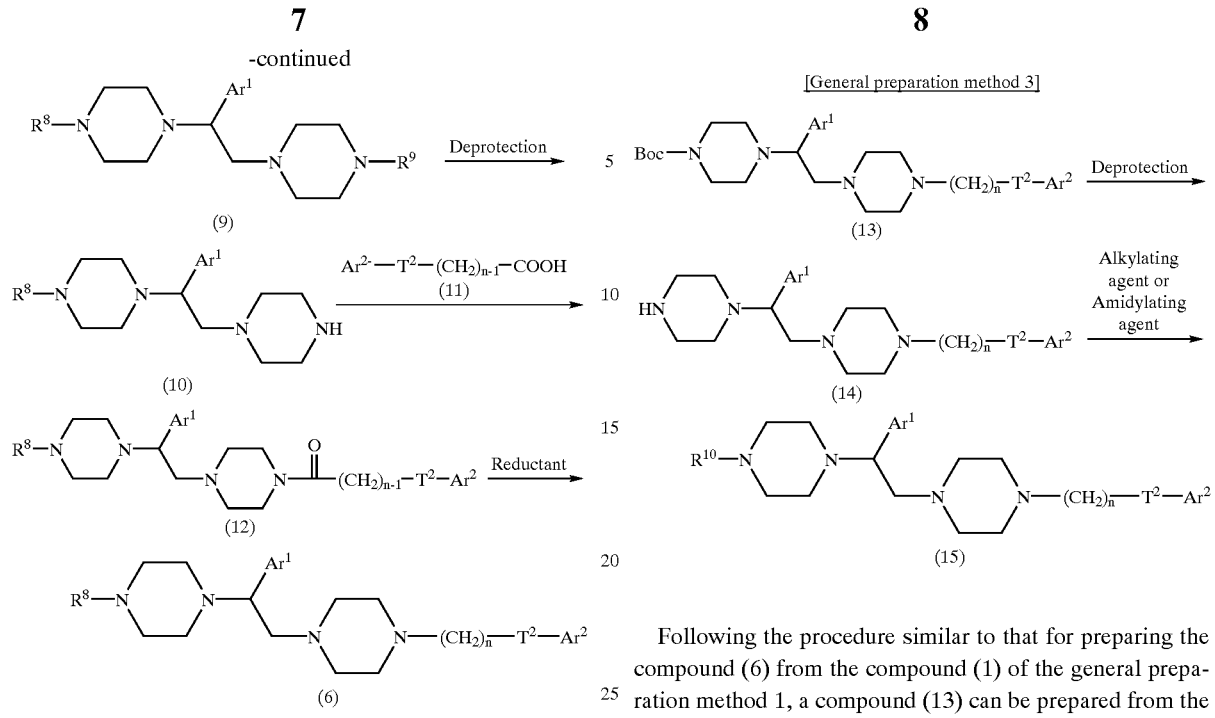

Following the procedure similar to that for preparing the compound (6) from the compound (1) of the general preparation method 1, a compound (9) can be prepared from the compound (1). Then, the amino group of the compound (9) can be deprotected to give a compound (10), which can be then condensed with a compound (11) in an inert solvent to give a compound (12). The amide group of the compound (12) can be reduced in an inert solvent to give a the compound (6) of the present invention.

The deprotection of the compound (9) can be carried out using the method described in Protective Groups in Organic Synthesis, by Theodora W. Greene and Peter G. M. Wuts. The condensation includes, for example, an amidation via an acid halide (e.g., an acid chloride and an acid bromide), an amidation via a mixed acid anhydride using ethyl chlorocarbonate, isobutyl chlorocarbonate, etc., and an amidation using a condensing agent such as 1-(3,3-dimethylaminopropyl)-3-ethylcarbodiimide, 1,3-dicyclohexylcarbodiimide, diphenylphosphoryl azide, diethyl cyanophosphate or carbonyldiimidazole. The reduction includes, for example, a reduction under an acidic, neutral or basic condition using a boron reductant (e.g., diborane) or an aluminum reductant (e.g. lithium aluminum hydride, Red-Al and diisopropyl aluminum hydride). The inert solvent include, for example, alcohols (e.g., methanol and ethanol), ethers (e.g., diethyl ether and tetrahydrofuran), hydrocarbons (e.g., toluene and benzene), halogenated carbon type solvents (e.g., chloroform and dichloromethane), dimethylformamide, acetonitrile, water and a mixture thereof.

Following the procedure similar to that for preparing the compound (6) from the compound (1) of the general preparation method 1, a compound (13) can be prepared from the compound (1). Removal of the Boc group of the compound (13) can give a compound (14) of the present invention. Then, the compound (14) can be reacted with an alkylating agent or an amidylating agent in the presence or absence of a base in an inert solvent to give a compound (15) of the present invention.

The removal of the Boc group of the compound (13) can be carried out according to the method described in Protective Groups in Organic Synthesis, by Theodora W. Greene and Peter G. M. Wuts. The alkylating agent include, for example, alkyl halides (e.g., methyl iodide, ethyl iodide, 1-bromopropane, 2-bromopropane and 2-bromopropionitrile), alkyl sulfates (e.g., dimethyl sulfate and diethyl sulfate). The amidylating agent includes, for example, an amidylating agent such as cyanamide, S-methylthiourea and aminoiminomethanesulfonic acid. The base include, for example, organic amines (e.g., triethylamine, diisopropylethylamine and pyridine) and inorganic bases (e.g., potassium carbonate, sodium bicarbonate, sodium hydroxide, potassium hydroxide and sodium hydride). The inert solvent include, for example, alcohols (e.g., methanol and ethanol), ethers (e.g., diethyl ether and tetrahydrofuran), hydrocarbons (e.g., toluene and benzene), halogenated carbon type solvents (e.g., chloroform and dichloromethane), dimethylformamide, acetonitrile, water and a mixture thereof.

[General preparation method 4]

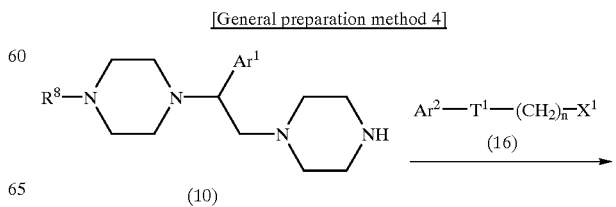

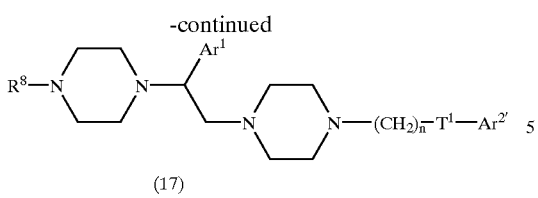

A compound (10) obtained according to the general preparation method 2 can be reacted with a compound (16) in the presence or absence of a base in an inert solvent to give a compound (17) of the present invention.

The base include, for example, organic amines (e.g., triethylamine, diisopropylethylamine and pyridine) and inorganic bases (e.g., potassium carbonate, sodium bicarbonate, sodium hydroxide, potassium hydroxide and sodium hydride). The inert solvent include, for example, alcohols (e.g., methanol and ethanol), ethers (e.g., diethyl ether and tetrahydrofuran), hydrocarbons (e.g., toluene and benzene), halogenated carbon type solvents (e.g., chloroform and dichloromethane), dimethylformamide, acetonitrile, water and a mixture thereof.

[General preparation method 5]

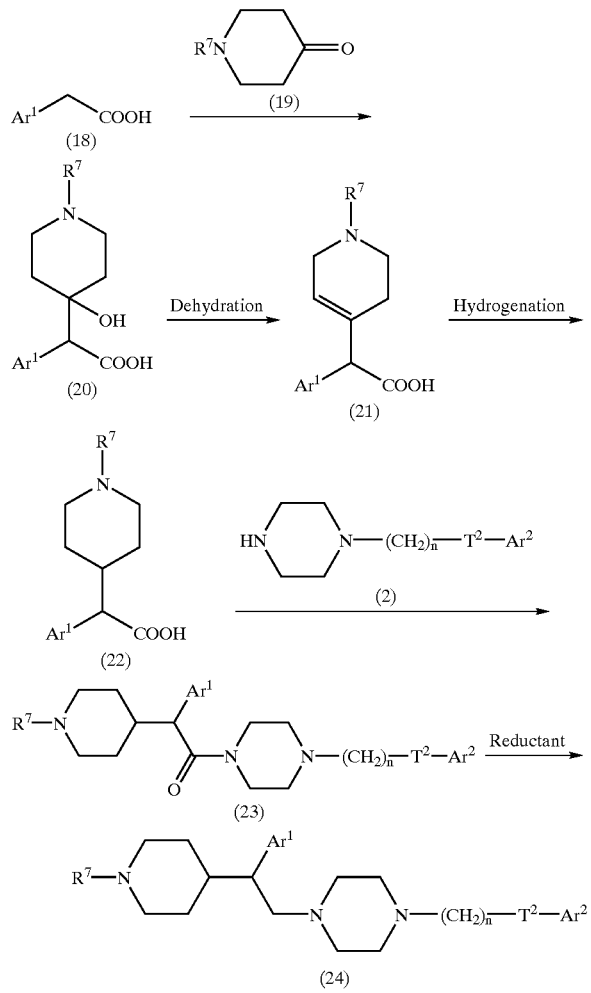

A compound (18) can be treated with a base in an inert solvent and reacted with a compound (19) to give a compound (20), which can be then treated with an acid in an inert solvent to synthesize a compound (21). The compound (21) can be hydrogenated in an inert solvent to give a compound (22), which can be then condensed with the compound (2) in an inert solvent to give a compound (23). The amide group of the compound (23) can be reduced in an inert solvent to a compound (24) of the present invention.

The base include, for example, metal amides (e.g., lithium diisopropylamide, lithium hexamethyldisilazide, sodium hexamethyldisilazide and potassium hexamethyldisilazide) and metal hydrides (e.g., sodium hydride and potassium hydride). The acid include, for example, inorganic acids (e.g., hydrochloric acid, hydrobromic acid, sulfuric acid, nitric acid and phosphoric acid) and organic acids (e.g., p-toluenesulfonic acid, methanesulfonic acid, trifluoroacetic acid and formic acid). The hydrogenation includes, for example, a reaction which is carried out in an inert solvent using a conventional metal catalyst (e.g., palladium-carbon, palladium-black, palladium hydroxide, platinum dioxide and Raney nickel) under a hydrogen atmosphere. The condensation include, for example, an amidation via an acid halide(e.g., an acid chloride and an acid bromide), an amidation via a mixed acid anhydride using ethyl chlorocarbonate, isobutyl chlorocarbonate, etc., and an amidation using a condensing agent such as 1-(3,3-dimethylaminopropyl)-3-ethylcarbodiimide, 1,3-dicyclohexylcarbodiimide, diphenylphosphoryl azide, diethyl cyanophosphate or carbonyldiimidazole. The reduction includes, for example, a reduction under an acidic, neutral or basic condition using a boron reductant (e.g. diborane) or an aluminum reductant (e.g. lithium aluminum hydride, Red-Al and diisobutyl aluminum hydride). The inert solvent include, for example, alcohols (e.g., methanol and ethanol), ethers (e.g., diethyl ether and tetrahydrofuran), hydrocarbons (e.g., toluene and benzene), halogenated carbon type solvents (e.g., chloroform and dichloromethane), dimethylformamide, acetonitrile, water and a mixture thereof.

[General preparation method 6]

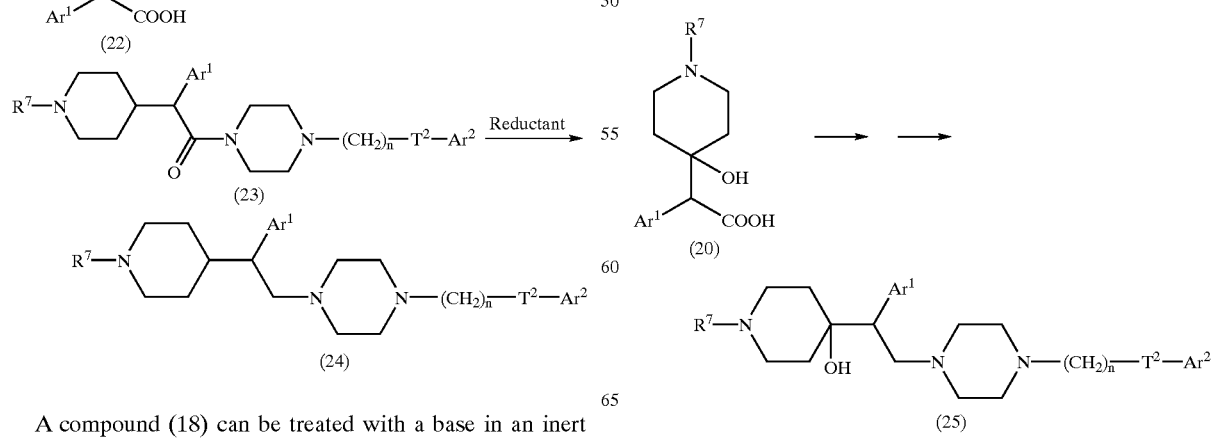

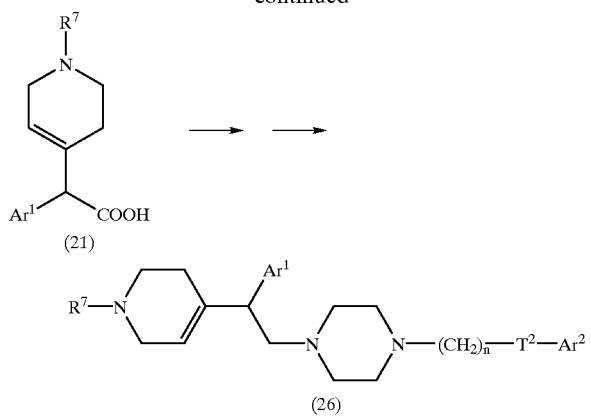

Following the procedure similar to that for preparing the compound (24) from the compound (22) of the general preparation method 5, a compound (25) of the present invention can be prepared from the compound (20), and a compound (26) of the present invention can be prepared from the compound (21).

[General preparation method 7]

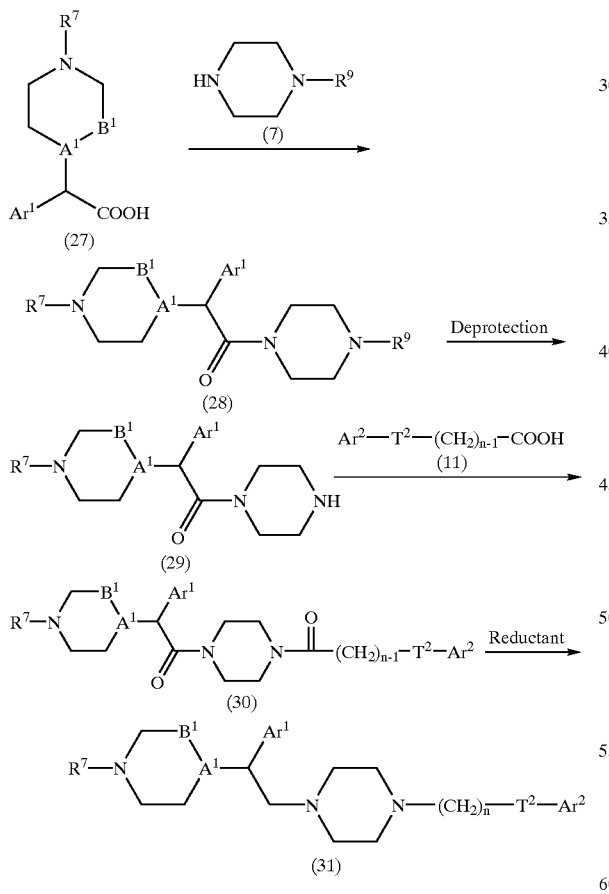

The compound (27) obtained by the general preparation method 5 can be condensed with the compound (7) in an inert solvent to give a compound (28), followed by deprotection of the amino group of the compound (28) to synthesize a compound (29). The compound (29) can be condensed with the compound (11) in an inert solvent to give a compound (30), followed by reduction of the amide group of the compound (30) in an inert solvent to give a compound (31) of the present invention.

The condensation include, for example, an amidation via an acid halide(e.g., an acid chloride and an acid bromide), an amidation via a mixed acid anhydride using ethyl chlorocarbonate, isobutyl chlorocarbonate, etc., and an amidation using a condensing agent such as 1-(3,3-dimethylaminopropyl)-3-ethylcarbodiimide, 1,3-dicyclohexylcarbodiimide, diphenylphosphoryl azide, diethyl cyanophosphate or carbonyldiimidazole. The deprotction of the compound (28) can be carried out according to the method described in Protective Groups in Organic Synthesis, by Theodora W. Greene and Peter G. M. Wuts. The reduction includes, for example, a reduction under an acidic, neutral or basic condition using a boron reductant (e.g. diborane) or an aluminum reductant (e.g. lithium aluminum hydride, Red-Al and diisobutyl aluminum hydride). The inert solvent include, for example, alcohols (e.g., methanol and ethanol), ethers (e.g., diethyl ether and tetrahydrofuran), hydrocarbons (e.g., toluene and benzene), halogenated carbon type solvents (e.g., chloroform and dichloromethane), dimethylformamide, acetonitrile, water and a mixture thereof.

[General preparation method 8]

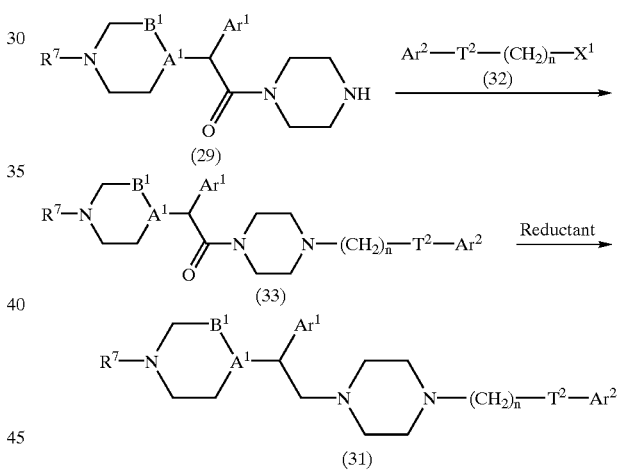

The compound (29) obtained according to the general preparation method 7 can be reacted with a compound (32) in the presence or absence of a base in an inert solvent to synthesize a compound (33). Reduction of the amide group of the compound (33) in an inert solvent can give a compound (31) of the present invention.

The base include, for example, organic amines (e.g., triethylamine, diisopropylethylamine and pyridine) and inorganic bases (e.g., potassium carbonate, sodium bicarbonate, sodium hydroxide, potassium hydroxide and sodium hydride). The reduction includes, for example, a reduction under an acidic, neutral or basic condition using a boron reductant (e.g., diborane) or an aluminum reductant (e.g. lithium aluminum hydride, Red-Al and diisobutyl aluminum hydride). The inert solvent include, for example, alcohols (e.g., methanol and ethanol), ethers (e.g., diethyl ether and tetrahydrofuran), hydrocarbons (e.g., toluene and benzene), halogenated carbon type solvents (e.g., chloroform and dichloromethane), dimethylformamide, acetonitrile, water and a mixture thereof.

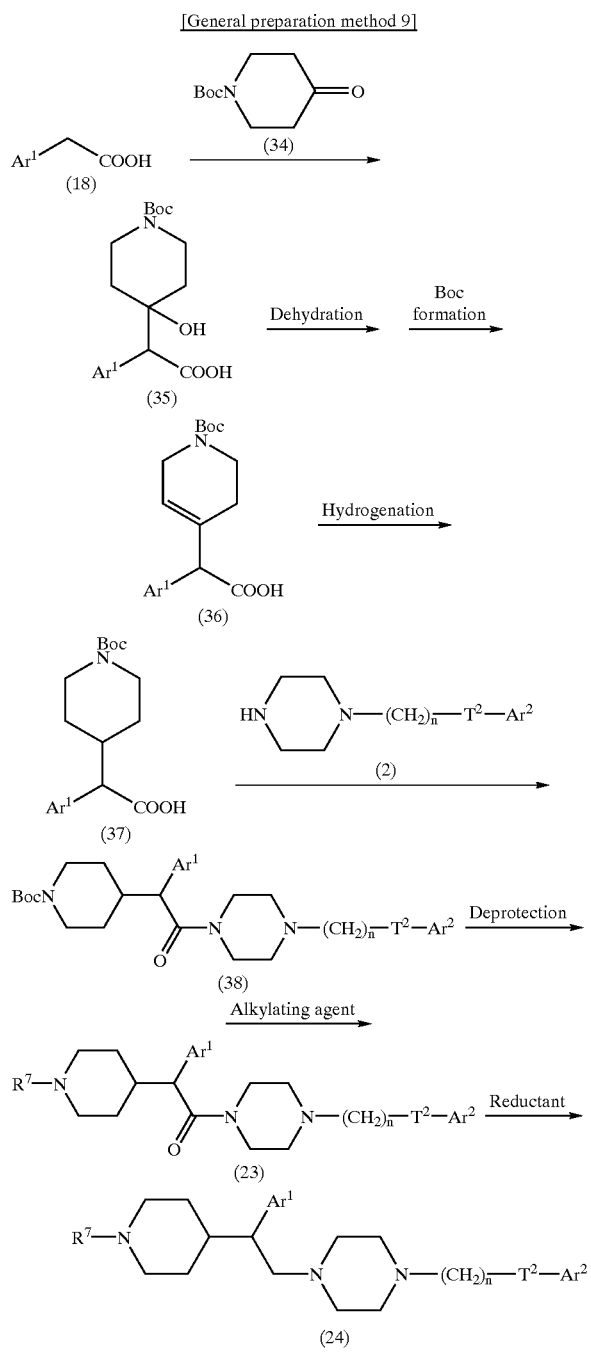

Following the procedure similar to that for preparing the compound (20) from the compound (18) of the general preparation method 5, a compound (35) can be prepared from the compound (18). Following the procedure similar to that for preparing the compound (21) from the compound (20) of the general preparation method 5 using the compound (35), and protecting the amino group again by a Boc group can give a compound (36). The compound (36) can be hydrogenated in an inert solvent to give a compound (37), which can be then condensed with the compound (2) in an inert solvent to give a compound (38). The Boc group of the compound (38) can be removed, followed by reaction with an alkylating agent in the presence or absence of a base in an inert solvent to synthesize the compound (23). The amide group of the compound (23) can be reduced in an inert solvent to give the compound (24) of the present invention.

Protection of the amino group by the Boc group or removal of the Boc group can be carried out according to the method described in Protective Groups in Organic Synthesis, by Theodora W. Greene and Peter G. M. Wuts. The hydrogenation is a reaction which is carried out in an inert solvent using a conventional metal catalyst (e.g., palladium-carbon, palladium-black, palladium hydroxide, platinum dioxide and Raney nickel) under a hydrogen atmosphere. The condensation include, for example, an amidation via an acid halide(e.g., an acid chloride or an acid bromide), an amidation via a mixed acid anhydride using ethyl chlorocarbonate, isobutyl chlorocarbonate, etc., and an amidation using a condensing agent such as 1-(3,3-dimethylaminopropyl)-3-ethylcarbodiimide, 1,3-dicyclohexylcarbodiimide, diphenylphosphoryl azide, diethyl cyanophosphate or carbonyldiimidazole. The base include, for example, organic amines (e.g., triethylamine, diisopropylethylamine and pyridine) and inorganic bases (e.g., potassium carbonate, sodium bicarbonate, sodium hydroxide, potassium hydroxide and sodium hydride). The alkylating agent include, for example, alkyl halides (e.g., methyl iodide, ethyl iodide, 1-bromopropane, 2-bromopropane or 2-bromopropionitrile) and alkyl sulfates (e.g., dimethyl sulfate or diethyl sulfate). The reduction includes, for example, a reduction under an acidic, neutral or basic condition using a boron reductant (e.g., diborane) or an aluminum reductant (e.g., lithium aluminum hydride, Red-Al and diisobutyl aluminum hydride). The inert solvent include, for example, alcohols (e.g., methanol and ethanol), ethers (e.g., diethyl ether and tetrahydrofuran), hydrocarbons (e.g., toluene and benzene), halogenated carbon type solvents (e.g., chloroform and dichloromethane), dimethylformamide, acetonitrile, water and a mixture thereof.

[General preparation method 10]

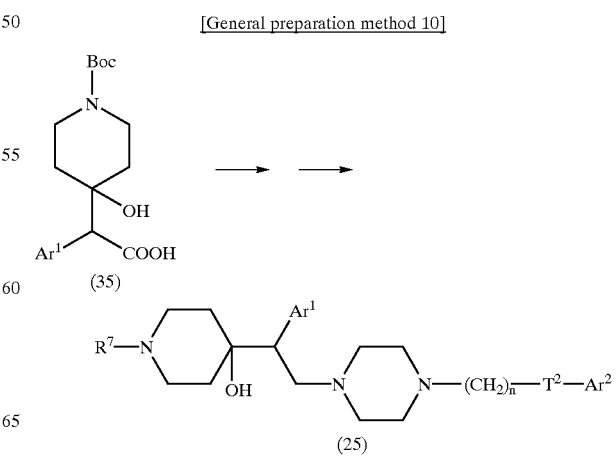

-continued

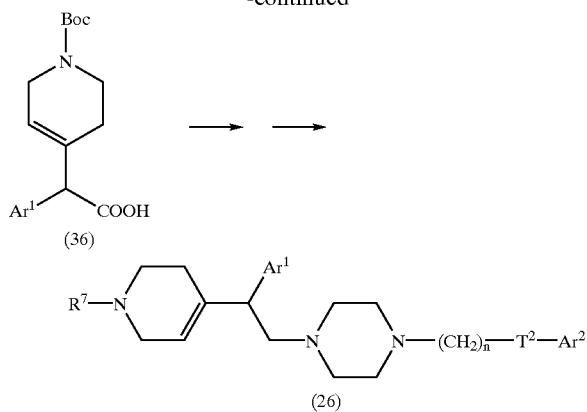

Following the procedure similar to that for preparing the compound (24) from the compound (37) of the general preparation method 9, the compound (25) and the compound (26) of the present invention can be prepared from the compound (35) and a compound (36), respectively.

[General preparation method 11]

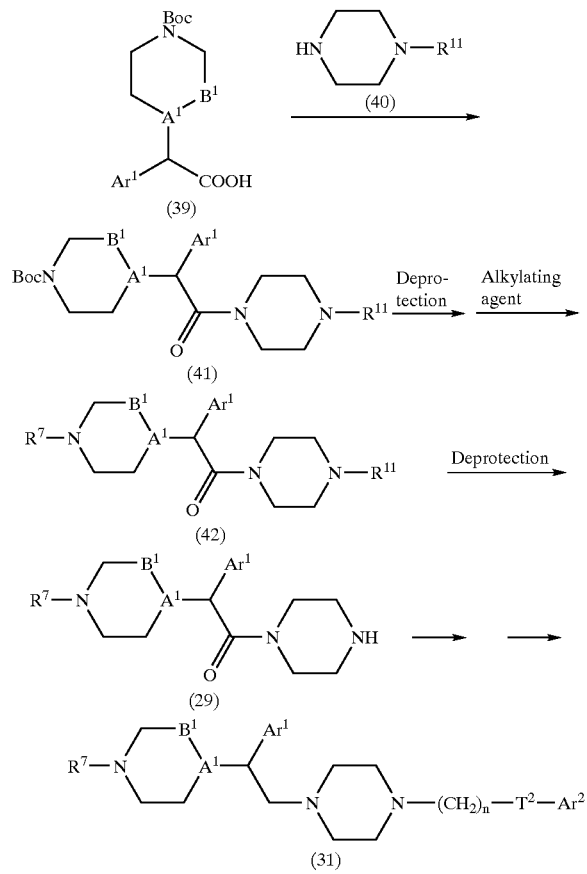

A compound (39) obtained by the general preparation method 9 can be condensed with a compound (40) in an inert solvent to give a compound (41), and the Boc group of the compound (41) can be removed, followed by reaction with an alkylating agent in the presence or absence of a base in an inert solvent to give the compound (42). The amino group of the compound (42) can be deprotected to synthesize the compound (26). Then, following the procedure similar to that from the compound (29) of the general preparation method 7 or similar to that of the general preparation method 8, a compound (31) of the present invention can be prepared.

The condensation include, for example, an amidation via an acid halide(e.g., an acid chloride, an acid bromide), an amidation via a mixed acid anhydride using ethyl chlorocarbonate, isobutyl chlorocarbonate, etc., and an amidation using a condensing agent such as 1-(3,3-dimethylaminopropyl)-3-ethylcarbodiimide, 1,3-dicyclohexylcarbodiimide, diphenylphosphoryl azide, diethyl cyanophosphate or carbonyldiimidazole. The base include, for example, organic amines (e.g., triethylamine, diisopropylethylamine and pyridine) and inorganic bases (e.g., potassium carbonate, sodium bicarbonate, sodium hydroxide, potassium hydroxide or sodium hydride). The alkylating agent include, for example, alkyl halides (e.g., methyl iodide, ethyl iodide, 1-bromopropane, 2-bromopropane or 2-bromopropionitrile), alkyl sulfates (e.g., dimethyl sulfate or diethyl sulfate). Removal of the Boc group or deprotection of the amino group can be carried out according to the method described in Protective Groups in Organic Synthesis, by Theodora W. Greene and Peter G. M. Wuts. The inert solvent includes, for example, alcohols (e.g., methanol and ethanol), ethers (e.g., diethyl ether and tetrahydrofuran), hydrocarbons (e.g., toluene and benzene), halogenated carbon type solvents (e.g., chloroform and dichloromethane), dimethylformamide, acetonitrile, water and a mixture thereof.

[General preparation method 12]

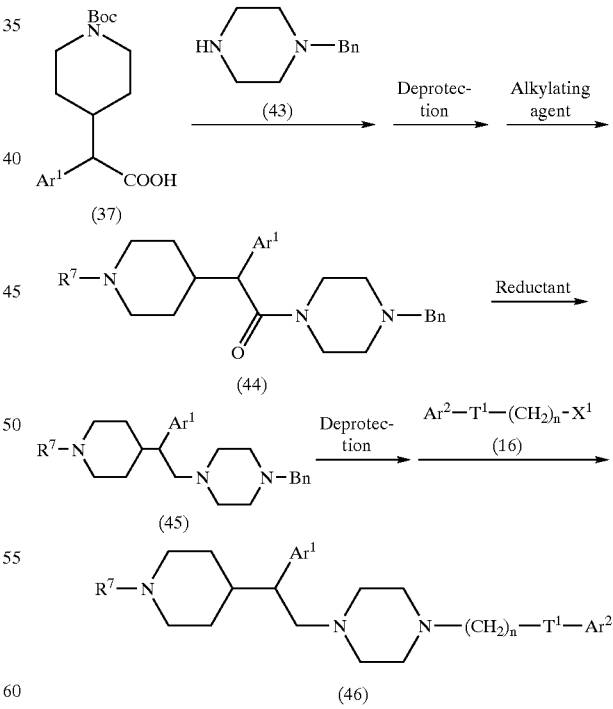

Following the procedure similar to that for preparing the compound (42) from the compound (39) of the general preparation method 11, a compound (44) can be prepared from the compound (37). Reduction of the amide group of the compound (44) in an inert solvent can give a compound (45), and the benzyl group of the compound (45) can be removed, followed by reaction with the compound (16) in the presence or absence of a base in an inert solvent to give a compound (46) of the present invention.

The reduction includes, for example, a reduction under an acidic, neutral or basic condition using a boron reductant (e.g., diborane) or an aluminum reductant (e.g. lithium aluminum hydride, Red-Al and diisobutyl aluminum hydride). Removal of the benzyl group can be carried out according to the method described in Protective Groups in Organic Synthesis, by Theodora W. Greene and Peter G. M. Wuts. The base include, for example, organic amines (e.g., triethylamine, diisopropylethylamine and pyridine) and inorganic bases (e.g., potassium carbonate, sodium bicarbonate, sodium hydroxide, potassium hydroxide and sodium hydride). The inert solvent include, for example, alcohols (e.g., methanol and ethanol), ethers (e.g., diethyl ether and tetrahydrofuran), hydrocarbons (e.g., toluene and benzene), halogenated carbon type solvents (e.g., chloroform and dichloromethane), dimethylformamide, acetonitrile, water and a mixture thereof.

[General Preparation Method 13]

Optically active compounds (6), (14), (15), (17), (24), (25), (26), (31) and (46) of the present invention can be obtained by optical resolution of racemic mixtures of (6), (14), (15), (17), (24), (25), (26), (31) and (46) of the present invention, respectively, by an ordinary optical resolution using an acidic chiral resolving agent or an optical resolution by HPLC using a chiral stationary phase. Further, an optically active compound (6) can be synthesized by resolving a racemic mixture of synthesis intermediate (4), (8), (9), (10) or (12) by an optical resolution using an acidic chiral resolving agent or an optical resolution by HPLC using a chiral stationary phase and following the method described in the general preparation method 1 or 2. Furthermore, an optically active compound (14) or (15) can be synthesized by resolving a racemic mixture of synthesis intermediate (13) by an optical resolution using an acidic chiral resolving agent or an optical resolution by HPLC using a chiral stationary phase and following the method described in the general preparation method 3. An optically active compound (17) can be synthesized by resolving a racemic mixture of synthesis intermediate (10) by an optical resolution using an acidic chiral resolving agent or an optical resolution by HPLC using a chiral stationary phase and following the method described in the general preparation method 4. An optically active compound (46) can be synthesized by resolving a racemic mixture of synthesis intermediate (45) by an optical resolution using an acidic chiral resolving agent or an optical resolution by HPLC using a chiral stationary phase and following the method described in the general preparation method 12.

The acidic chiral resolving agent includes, for example, optically active organic acids such as (+) or (−)-di-p-toluoyltartaric acid, (+) or (−)-dibenzoyltartaric acid, (+) or (−)-tartaric acid, (+) or (−)-mandelic acid, (+) or (−)-camphoric acid, or (+) or (−)-camphor-sulfonic acid.

The chiral stationary phase includes, for example, cellulose ester, cellulose carbamate, amylose carbamate, crown ether or polymethacrylate or derivatives thereof.

[General preparation method 14]

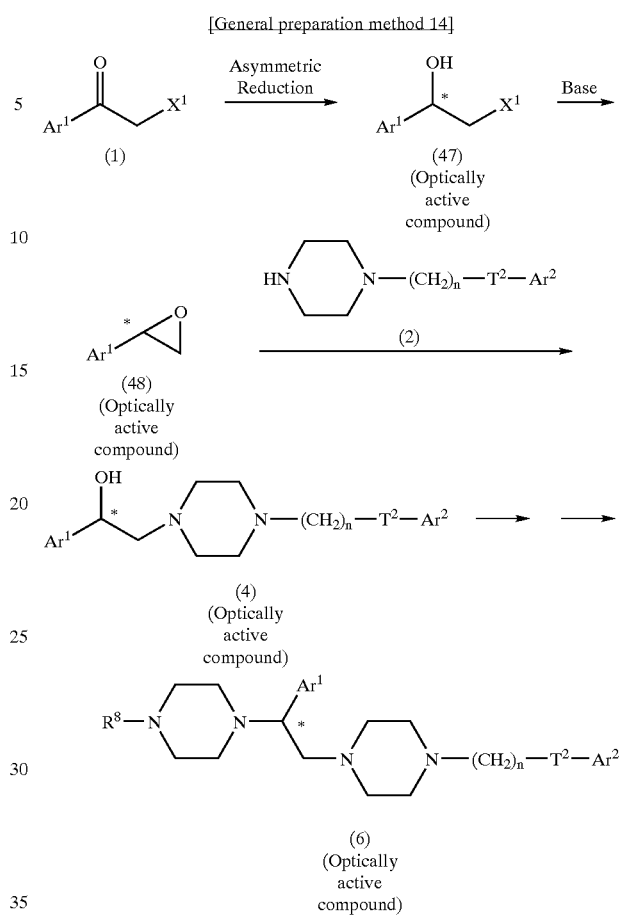

The compound (1) can be subjected to asymmetric reduction in an inert solvent to give an optically active alcohol (47). The compound (47) can be subjected to epoxidation in the presence or absence of a base in an inert solvent, and then reacted with the compound (2) in an inert solvent to synthesize an optically active compound (4). Then, following the procedure similar to that for preparing the compound (6) from the compound (4) of the general preparation method 1, an optically active compound (6) of the present invention can be prepared from the optically active compound (4).

The asymmetric reduction includes, for example, a reduction by borane-tetrahydrofuran complex using oxazaborolidines such as (R)-5,5-diphenyl-2-methyl-3,4-propano-1,3,2-oxazaborolidine or (S)-5,5-diphenyl-2-methyl-3,4-propano-1,3,2-oxazaborolidine as a chiral auxiliary group, a reduction using optically active metal hydrides such as (R)-B-3-pinanyl-9-borabicyclo-[3.3.1]nonane, (S)-B-3-pinanyl-9-borabicyclo-[3.3.1]nonane, (−)-chlorodiisopinocamphenylborane, (+)-chlorodiisopinocamphenylborane, (R,R)-2,5-dimethylborane, (S,S)-2,5-dimethylborane, (R)-BINAL-H and (S)-BINAL-H, or an asymmetric hydrogenation using an optically active metal catalyst such as optically active BINAP-ruthenium complex. The base include, for example, organic amines (e.g., triethylamine, diisopropylethylamine and pyridine), inorganic bases (e.g., potassium carbonate, sodium bicarbonate, sodium hydroxide, potassium hydroxide and sodium hydride), metal amides (e.g., lithium diisopropylamide, lithium hexamethyldisilazide, sodium hexamethyldisilazide or potassium hexamethyldisilazide) and metal hydrides (e.g., sodium hydride and potassium hydride). Examples of the inert solvent include, for example, alcohols (e.g., methanol and ethanol), ethers (e.g., diethyl ether and tetrahydrofuran), hydrocarbons (e.g., toluene and benzene), halogenated carbon type solvents (e.g., chloroform and dichloromethane), dimethylformamide, acetonitrile, water and a mixture thereof.

[General preparation method 15]

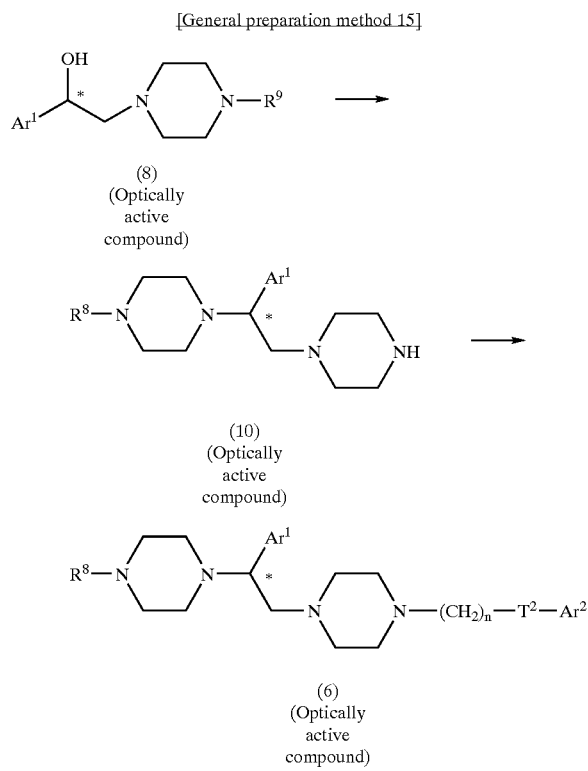

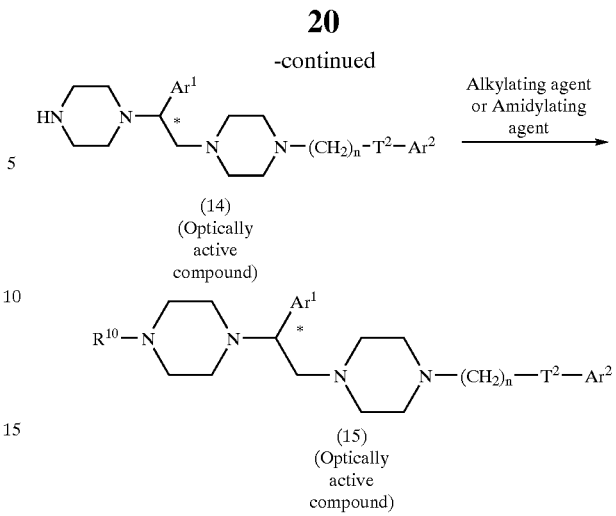

Following the procedure similar to that for preparing the compound (6) from the compound (1) of the general preparation method 14, an optically active compound (13) can be prepared from the compound (1). Then, following the procedure similar to that of the general preparation method 3, optically active compounds (14) and (15) of the present invention can be prepared from the optically active compound (13).

[General preparation 17]

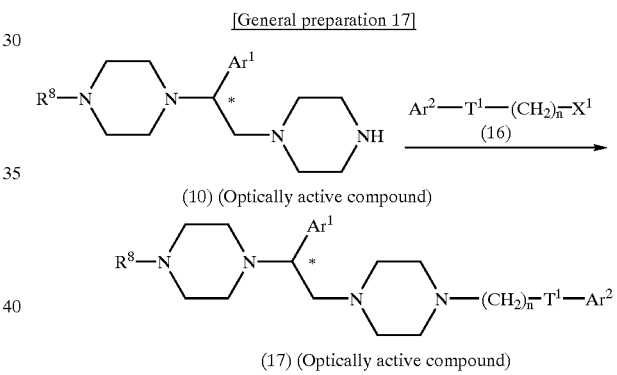

Following the procedure similar to that for preparing the compound (4) from the compound (1) of the general preparation method 14, an optically active compound (8) can be prepared from the compound (1). Then, following the procedure similar to that for preparing the compound (6) from the compound (8) of the general preparation method 2, an optically active compound (6) can be prepared from the optically active compound (8).

[General preparation method 16]

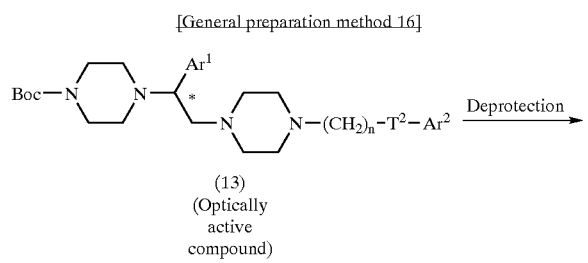

Following the procedure similar to that of the general preparation method 4, an optically active compounds (17) can be prepared from an optically active compound (10) which can be obtained by the general preparation method 15.

The compounds of the present invention can be administered orally or parenterally, and the dosage forms thereof are, for example, tablets, capsules, granules, fine-powders, powders, troches, ointments, creams, emulsions, suspensions, suppositories and injections, all of which can be prepared by conventional preparation techniques (e.g., the method defined in Japanese Pharmacopoeia, 12th edition). These dosage forms can be suitably chosen according to conditions and age of the patient and the purpose of therapy. These forms can be prepared by using conventional excipients (e.g., crystalline cellulose, starches, lactose and mannitol), binders (e.g., hydroxypropylcellulose and polyvinylpyrrolidone), lubricants (e.g., magnesium stearate and talc), disintegrators (e.g., carboxymethylcellulose calcium).

The dose of the compound of the present invention for the treatment of adult human may range from 1 to 2000 mg per day, in a single portion or several divided portions, and can be suitably increased or decreased depending on age, body weight and conditions of the patient.

MODE FOR CARRYING OUT THE INVENTION

The present invention is illustrated in more detail by the following examples and experiments.

EXAMPLE 1

Synthesis of 1-[2-(4-methoxyphenyl)-2-(4-methylpiperazino)ethyl]-4-(4-naphthalen-1-yl-butyl)piperazine trimaleate (Compound 32 in Table 1)

(1) In 6.0 ml of chloroform was dissolved 0.69 g of 4-methoxyphenacyl bromide, and 3.0 ml of N-ethyldiisopropylamine and 1.20 g of 1-(4-naphthalen-1-yl-butyl)piperazine dihydrochloride were added, followed by reflux with heating for an hour. The reaction solution was cooled to room temperature, and concentrated under reduced pressure. To the residue was added a saturated aqueous sodium bicarbonate solution and, after extraction with ethyl acetate, the organic layer was dried over anhydrous sodium sulfate. After removal of the drying agent by filtration, the filtrate was concentrated under reduced pressure to give a crude 1-[2-(4-methoxyphenyl)-2-oxoethyl]-4-(4-naphthalen-1-yl-butyl)piperazine.

(2) The crude 1-[2-(4-methoxyphenyl)-2-oxoethyl]-4-(4-naphthalen-1-yl-butyl)piperazine obtained in (1) was dissolved in 10 ml of ethanol, and then a solution prepared by adding 1 drop of 10% aqueous potassium hydroxide solution and 0.18 g of sodium borohydride to 1.0 ml of water was added, followed by stirring at 50° C. for an hour. To the reaction solution was poured water and, after extraction with ethyl acetate, the organic layer was dried over anhydrous sodium sulfate. After removal of the drying agent by filtration, the filtrate was concentrated under reduced pressure to give a crude 1-[2-hydroxy-2-(4-methoxyphenyl)ethyl]-4-(4-naphthalen-1-yl-butyl)piperazine.

(3) The crude 1-[2-hydroxy-2-(4-methoxyphenyl)ethyl]-4-(4-naphthalen-1-yl-butyl)piperazine obtained in (2) and 1.25 ml of triethylamine were dissolved in 10 ml of methylene chloride and, after ice-cooling, 0.46 ml of methanesulfonyl chloride was added, followed by stirring at room temperature for 30 minutes. To the reaction solution were added 0.84 ml of triethylamine and 1.0 ml of 1-methylpiperazine, successively, followed by stirring at room temperature for 3 hours. After concentration of the reaction solution under reduced pressure, a saturated aqueous sodium bicarbonate solution was poured and, after extraction with ethyl acetate, the organic layer was dried over anhydrous sodium sulfate. After removal of the drying agent by filtration, the filtrate was concentrated under reduced pressure, and the residue was purified by a silica gel column chromatography (Chromatorex NH, hexane:ethyl acetate=1:1) to give 0.94 g of 1-[2-(4-methoxyphenyl)-2-(4-methylpiperazino)ethyl]-4-(4-naphthalen-1-yl-butyl)piperazine.

(4) 0.94 g of 1-[2-(4-Methoxyphenyl)-2-(4-methylpiperazino)ethyl]-4-(4-naphthalen-1-yl-butyl)piperazine was dissolved in 5.0 ml of ethanol, 5.0 ml of an ethanol solution of 0.56 g of maleic acid was added, followed by being allowed to stand for 2 hours. The precipitated crystals were collected by filtration and washed with ethanol to give 1.24 g of 1-[2-(4-methoxyphenyl)-2-(4-methylpiperazino)ethyl]-4-(4-naphthalen-1-yl-butyl)piperazine trimaleate as crystals.

The structures and physical property data of the present compound and the compounds prepared similarly are shown in Tables 1 and 2.

EXAMPLE 2

Synthesis of 1-[2-(4-fluorophenyl)-2-(4-methylpiperazino)ethyl]-4-(4-naphthalen-1-yl-butyl)piperazine tetrahydrochloride (Compound 4 in Table 1)

(1) 4.3 g of 2-Chloro-4'-fluoroacetophenone and 8.0 g of 1-ethoxycarbonylpiperazine were dissolved in 30 ml of chloroform and refluxed with heating for 2 hours. After cooling to room temperature, the reaction solution was concentrated under reduced pressure, and 25% aqueous ammonia solution was added, followed by extraction with ether. The organic layer was dried over anhydrous sodium sulfate. After removal of the drying agent by filtration, the filtrate was concentrated under reduced pressure to give a crude 1-ethoxycarbonyl-4-[2-(4-fluorophenyl)-2-oxoethyl]piperazine, which was then dissolved in 40 ml of ethanol, and a solution prepared by adding 1 drop of 5% potassium hydroxide and 1.0 g of sodium borohydride to 5 ml of water was added, followed by heating at 50° C. for an hour. After concentration of the reaction solution under reduced pressure, water was added, followed by extraction with ether, and the organic layer was dried over anhydrous sodium sulfate. After removal of the drying agent by filtration, the filtrate was concentrated under reduced pressure. To the residue was poured 50 ml of 4M hydrogen chloride/ethyl acetate solution, the solution was concentrated under reduced pressure, and the resulting solid was washed with ether to give 8.3 g of 1-ethoxycarbonyl-4-[2-(4-fluorophenyl)-2-hydroxyethyl]piperazine hydrochloride.

(2) To 8.3 g of 1-ethoxycarbonyl-4-[2-(4-fluorophenyl)-2-hydroxyethyl]piperazine hydrochloride were added 20 ml of benzene and 2.5 ml of thionyl chloride, followed by heating at 50° C. for 10 minutes. The reaction solution was concentrated under reduced pressure, 25% aqueous ammonia solution and water were poured, followed by extraction with ethyl acetate. The organic layer was dried over anhydrous sodium sulfate and, after removal of the drying agent by filtration, the filtrate was concentrated under reduced pressure. To the residue was poured 50 ml of 4M hydrogen chloride/ethyl acetate solution, the solution was concentrated under reduced pressure, and the resulting solid was washed with ether to give 8.1 g of 1-ethoxycarbonyl-4-[2-chloro-2-(4-fluorophenyl)ethyl]-piperazine hydrochloride.

(3) To 7.6 g of 1-ethoxycarbonyl-4-[2-chloro-2-(4-fluorophenyl)ethyl]piperazine hydrochloride were poured 5 ml of 25% aqueous ammonia solution and water and, after extraction with ether, the organic layer was dried over anhydrous sodium sulfate. After removal of the drying agent by filtration, the filtrate was concentrated under reduced pressure. The residue was dissolved in 20 ml of benzene, and 5.4 ml of 1-methylpiperazine was added, followed by heating at 65° C. for 3.5 hours. To the reaction solution were poured 25% aqueous ammonia solution and water and, after extraction with ether, the organic layer was dried over anhydrous sodium sulfate. After removal of the drying agent by filtration, the filtrate was concentrated under reduced pressure. The residue was purified by a silica gel column chromatography (Chromatorex NH, hexane:ethyl acetate= 4:1) to give 6.58 g of 1-ethoxycarbonyl-4-[2-(4-fluorophenyl)-2-(4-methylpiperazino)ethyl]piperazine as an oil.

(4) 1.25 g of 1-Ethoxycarbonyl-4-[2-(4-fluorophenyl)-2-(4-methylpiperazino)ethyl]piperazine was dissolved in 2 ml of ethanol, and 1.3 g of potassium hydroxide was added, followed by reflux with heating for an hour. The reaction solution was cooled to room temperature and, after addition of 2 ml of water, extracted with ethyl acetate, and the organic layer was dried over anhydrous sodium sulfate. After removal of the drying agent by filtration, the filtrate was concentrated under reduced pressure to give 1.0 g of a crude 1-[2-(4-fluorophenyl)-2-(4-methyl-piperazino)ethyl] piperazine.

(5) 0.37 g of 4-Naphthalen-1-yl-butyric acid was dissolved in 5.0 ml of toluene, and 0.35 ml of thionyl chloride and 1 drop of dimethylformamide were added, followed by heating at 70° C. for 30 minutes. The reaction solution was cooled to room temperature and concentrated under reduced pressure to give a crude 4-naphthalen-1-yl-butyryl chloride. To the resulting crude 4-naphthalen-1-yl-butyryl chloride was added 2.3 ml of a toluene solution of 0.40 g of 1-[2-(4-fluorophenyl)-2-(4-methylpiperazino)ethyl] piperazine, followed by stirring at room temperature for 30 minutes. To the reaction solution was added a saturated aqueous sodium bicarbonate solution and, after extraction with ethyl acetate, the organic layer was dried over anhydrous sodium sulfate. After removal of the drying agent by filtration, the filtrate was concentrated under reduced pressure, and the residue was purified by a silica gel column chromatography (Wako-gel C-200, chloroform:methanol= 10:1) to give 0.58 g of 1-[2-(4-fluorophenyl)-2-(4-methylpiperazino)ethyl]-4-(4-naphthalen-1-yl-butyryl) piperazine as an oil.

(6) 0.32 of 1-[2-(4-Fluorophenyl)-2-(4-methylplperazlno)ethyl]-4-(4-naphthalen-1-yl-butyryl)piperazine was dissolved in 10 ml of tetrahydrofuran, and 50 mg of lithium aluminuni hydride was added, followed by reflux with heating for 30 minutes. The reaction solution was cooled to room temperature and, after addition of 1 ml of 10% aqueous sodium hydroxide solution, ether was added, followed by drying over anhydrous sodium sulfate. After removal the drying agent by filtration, the filtrate was concentrated under reduced pressure, and the residue was purified by silica gel column chromatography (Chromatorex NH, hexane:ethyl acetate=1:1) to give 0.30 g of 1-[2-(4-fluorophenyl)-2-(4-methylpiperazino)ethyl]-4-(4-naphthalen-1-yl-butyl)piperazine as an oil.

(7) 0.30 g of 1-[2-(4-Fluorophenyl)-2-(4-methylpiperazino)ethyl]-4-(4-naphthalen-1-yl-butyl) piperazine was dissolved in 4 ml of methanol, and 1 ml of 4M hydrogen chloride/ethyl acetate solution was added. The solution was concentrated under reduced pressure, and the resulting solid was washed with methanol to give 1-[2-(4-fluorophenyl)-2-(4-methylpiperazino)ethyl]-4-(4-naphthalen-1-yl-butyl)piperazine tetrahydrochloride (0.20 g).

The structures and physical property data of the present compound and the compounds prepared similarly are shown in Tables 1 and 2.

EXAMPLE 3

Synthesis of 1-[2-(4-fluorophenyl)-2-(4-isopropylpiperazino)ethyl]-4-(4-naphthalen-1-yl-butyl) piperazine trimaleate (Compound 16 in Table 1)

(1) 0.62 g of 1-[2-(4-Fluorophenyl)-2-(4-t-butoxycarbonylpiperazino)ethyl]-4-(4-naphthalen-1-yl-butyl)piperazine was dissolved in a mixture of 3 ml of ethyl acetate and 3 ml of methanol, and 4 ml of 4M hydrogen chloride/ethyl acetate solution was added, followed by stirring at room temperature for 6 hours. The precipitated crystals were collected by filtration, and the crystals were washed with ethyl acetate to give 0.42 g of 1-[2-(4-fluorophenyl)-2-piperazinoethyl]-4-(4-naphthalen-1-yl-butyl)piperazine tetrahydrochloride as an oil.

(2) 0.2 g of 1-[2-(4-Fluorophenyl)-2-piperazinoethyl]-4-(4-naphthalen-1-yl-butyl)piperazine tetrahydrochloride was dissolved in 0.7 ml of dimethylformamide, and 74 mg of 60% sodium hydride in oil was added with ice-cooling. The temperature was elevated to room temperature, followed by stirring for 10 minutes. To the reaction solution was added a 0.3 ml of dimethylformamide solution of 0.2 g of 2-bromopropane, followed by stirring overnight. The reaction solution was poured to water and, after extraction with ethyl acetate, the organic layer was washed with a saturated aqueous sodium chloride solution and dried over anhydrous sodium sulfate. After removal of the drying agent by filtration, the filtrate was concentrated under reduced pressure, and the residue was purified by a silica gel column chromatography (Chromatorex NH, hexane:ethyl acetate= 1:1) to give 0.13 g of 1-[2-(4-fluorophenyl)-2-(4-isopropylpiperazino)ethyl]-4-(4-naphthalen-1-yl-butyl) piperazine as an oil.

(3) 0.13 g of 1-[2-(4-Fluorophenyl)-2-(4-isopropylpiperazino)ethyl]-4-(4-naphthalen-1-yl-butyl) piperazine was dissolved in 1.5 ml of ethanol, and 1 ml of an ethanol solution of 0.11 g of maleic acid was added, followed by allowing to stand for 2 hours. The precipitated crystals were collected by filtration and washed with ethanol to give 0.18 g of 1-[2-(4-fluorophenyl)-2-(4-isopropylpiperazino)ethyl]-4-(4-naphthalen-1-yl-butyl) piperazine trimaleate as crystals.

The structures and physical property data of the present compound and the compounds prepared similarly are shown in Table 1.

EXAMPLE 4

Synthesis 4-{1-(4-fluorophenyl)-2-[4-(4-naphthalen-1-yl-butyl)piperazin-1-yl]ethyl}piperazine-1-carboxamidine trimaleate (Compound 20 in Table 1)

0.72 g of 1-[2-(4-Fluorophenyl)-2-piperazinoethyl]-4-(4-naphthalen-1-yl-butyl)piperazine tetrahydrochloride obtained in Example 3(1) was dissolved in 10 ml of ethanol, and 0.20 g of cyanamide was added, followed by reflux with stirring for 4 hours. After cooling to room temperature, the reaction solution was concentrated under reduced pressure, a saturated aqueous sodium bicarbonate solution was added and, after extraction with ethyl acetate, the organic layer was dried over anhydrous sodium sulfate. After removal of the drying agent by filtration, the filtrate was concentrated under reduced pressure. The residue was dissolved in 3.0 ml of ethanol, and 3.0 ml of an ethanol solution of 0.50 g of maleic acid was added, followed by allowing to stand for 2 hours. The precipitated crystals were collected by filtration and washed with ethanol to give 0.52 g of 4-{1-(4-fluorophenyl)-2-[4-(4-naphthalen-1-yl-butyl)piperazin-1-yl]ethyl}piperazine-1-carboxamidine trimaleate as crystals.

The structures and physical property data of the present compound and the compounds prepared similarly are shown in Table 1.

EXAMPLE 5

Synthesis of 1-[2-(4-aminophenyl)-2-(4-methylpiperazino)ethyl]-4-(4-naphthalen-1-yl-butyl) piperazine trimaleate (Compound 39 in Table 1)

0.54 g of 1-[2-(4-Nitrophenyl)-2-(4-methylpiperazino) ethyl]-4-(4-naphthalen-1-yl-butyl)piperazine trimaleate obtained by the procedure similar to that of Example 1 was dissolved in 1M aqueous sodium hydroxide solution and extracted with chloroform. The organic layer was dried over anhydrous sodium sulfate. After removal of the drying agent by filtration, the filtrate was concentrated under reduced pressure. The residue was dissolved in 20 ml of ethanol, and 10 mg of platinum oxide was added, followed by stirring under a hydrogen atmosphere for 2 hours. After removal of the platinum oxide by filtration, the filtrate was concentrated under reduced pressure. The residue was dissolved in 3.0 ml of ethanol, and 3.0 ml of an ethanol solution of 0.19 g of maleic acid was added, followed by allowing to stand for 2 hours. The precipitated crystals were collected by filtration and washed with ethanol to give 0.35 g of 1-[2-(4-aminophenyl)-2-(4-methylpiperazino)ethyl]-4-(4-naphthalen-1-yl-butyl)piperazine trimaleate as crystals.

The structures and physical property data of the present compound and the compounds prepared similarly are shown in Table 1.

EXAMPLE 6

Synthesis of 1-[2-(4-fluorophenyl)-2-(4-methylpiperazino)ethyl]-4-[4-(6-fluoro-1,2-benzisoxazol-3-yl)butyl]piperazine trimaleate (Compound 46 in Table 1)

(1) 0.37 g of 1-[2-(4-Fluorophenyl)-2-(4-methylpiperazino)ethyl]piperazine obtained in Example 2 (4) was dissolved in 4.0 ml of dimethylformamide, and 0.19 g of N-ethyldiisopropylamine and 0.31 g of 4-(6-fluoro-1,2-benzisoxazol-3-yl)butyl chloride were added, followed by stirring at 120° C. for 3 hours. The reaction solution was cooled to room temperature, diluted with ethyl acetate and washed with water and a saturated aqueous sodium chloride solution. The organic layer was dried over anhydrous sodium sulfate. After removal of the drying agent by filtration, the filtrate was concentrated under reduced pressure. The residue was purified by a silica gel column chromatography (Chromatorex NH, hexane:ethyl acetate= 1:1) to give 0.22 g of 1-[2-(4-fluorophenyl)-2-(4-methylpiperazino)ethyl]-4-[4-(6-fluoro-1,2-benzisoxazol-3-yl)butyl]piperazine as an oil.

(2) 0.21 g of 1-[2-(4-Fluorophenyl)-2-(4-methylpiperazino)ethyl]-4-[4-(6-fluoro-1,2-benzisoxazol-3-yl)butyl]piperazine was dissolved in 2.0 ml of ethanol, and 2.0 ml of an ethanol solution of 0.16 g of maleic acid was added, followed by allowing to stand for 2 hours. The precipitated crystals were collected by filtration and washed with ethanol to give 0.30 g of 1-[2-(4-fluorophenyl)-2-(4-methylpiperazino)ethyl]-4-[4-(6-fluoro-1,2-benzisoxazol-3-yl)butyl]piperazine trimaleate as crystals.

The structures and physical property data of the present compound and the compounds prepared similarly are shown in Tables 1 and 2.

EXAMPLE 7

Synthesis of 1-[2-(4-fluorophenyl)-2-(4-isopropylpiperazino)ethyl]-4-[4-(2-hydroxynaphthalen-1-yl)butyl]piperazine trimaleate (Compound 55 in Table 1)

0.06 g of 1-[2-(4-Fluorophenyl)-2-(4-isopropylpiperazino)ethyl]-4-[4-(2-methoxynaphthalen-1-yl)butyl]piperazine obtained by the procedure similar to that of Example 2 was dissolved in 10 ml of 48% aqueous hydrobromic acid solution and refluxed with heating for 2 hours. The reaction solution was cooled to room temperature and concentrated under reduced pressure, and 1M aqueous sodium hydroxide solution was added, followed by extraction with ether. The organic layer was dried over anhydrous sodium sulfate. After removal of the drying agent by filtration, the filtrate was concentrated under reduced pressure. The residue was purified by a silica gel column chromatography (Chromatorex NH, hexane:ethyl acetate= 1:1) to give 0.06 g of 1-[2-(4-fluorophenyl)-2-(4-isopropylpiperazino)ethyl]-4-[4-(2-hydroxynaphthalen-1-yl)butyl]piperazine as an oil.

The structures and physical property data of the present compound and the compounds prepared similarly are shown in Table 1.

EXAMPLE 8

Synthesis of 1-[2-(4-fluorophenyl)-2-(4-isopropylpiperazino)ethyl]-4-[4-(2-isopropoxynaphthalen-1-yl)butyl]piperazine trimaleate (Compound 56 in Table 1)

(1) 0.05 g of 1-[2-(4-Fluorophenyl)-2-(4-isopropylpiperazino)ethyl]-4-[4-(2-hydroxynaphthalen-1-yl)butyl]piperazine obtained in Example 7 was dissolved in 5 ml of dimethylformamide, and 0.19 g of potassium carbonate and 0.068 ml of 2-iodopropane were added, followed by stirring at 70° C. for 6 hours. The reaction solution was cooled to room temperature, diluted with ethyl acetate, and washed with water and a saturated aqueous sodium chloride solution. The organic layer was dried over anhydrous sodium sulfate. After removal of the drying agent by filtration, the filtrate was concentrated under reduced pressure. The residue was purified by a silica gel column chromatography (Chromatorex NH, hexane:ethyl acetate= 1:1) to give 0.03 g of 1-[2-(4-fluorophenyl)-2-(4-isopropylpiperazino)ethyl]-4-[4-(2-isopropoxynaphthalen-1-yl)butyl]piperazine as an oil.

(2) 0.03 g of 1-[2-(4-Fluorophenyl)-2-(4-isopropylpiperazino)ethyl]-4-[4-(2-isopropoxy-naphthalen-1-yl)butyl]piperazine was dissolved in 2.0 ml of ethanol, and 2.0 ml of an ethanol solution of 0.02 g of maleic acid was added, followed by allowing to stand for 2 hours. The precipitated crystals were collected by filtration and washed with ethanol to give 0.03 g of 1-[2-(4-fluorophenyl)-2-(4-isopropylpiperazino)ethyl]-4-[4-(2-isopropoxynaphthalen-1-yl)butyl]piperazine trimaleate as crystals.

The structures and physical property data of the present compound and the compounds prepared similarly are shown in Tables 1.

EXAMPLE 9

Synthesis of 1-[2-(4-carbamoylphenyl)-2-(4-isopropylpiperazino)ethyl]-4-[4-(2-methoxynaphthalen-1-yl)butyl]piperazine tetrahydrochloride (Compound 75 in Table 1)

(1) 0.50 g of 1-[2-(4-Methoxycarbonylphenyl)-2-(4-isopropylpiperazino)ethyl]-4-[4-(2-methoxynaphthalen-1-yl-butyl)piperazine obtained by the procedure similar to that of Example 2 was dissolved in 2 ml of conc. hydrochloric acid, and stirred at 80° C. for hours. The reaction solution was cooled to room temperature and concentrated under reduced pressure. The residue was suspended in 5 ml of thionyl chloride and refluxed with heating for 2 hours. After concentration of the reaction solution under reduced pressure, the residue was dissolved in 2.5 ml of tetrahydrofuran, and 25% aqueous ammonia solution was added, followed by stirring at room temperature for an hour. The reaction solution was diluted with ethyl acetate and washed with a saturated aqueous sodium bicarbonate solution and a saturated aqueous sodium chloride solution. The organic layer was dried over anhydrous sodium sulfate. After removal of the drying agent by filtration, the filtrate was concentrated under reduced pressure. The residue was purified by a silica gel column chromatography (Chromatorex NH, hexane:ethyl acetate=1:1) to give 0.10 g of 1-[2-(4-carbamoylphenyl)-2-(4-isopropylpiperazino) ethyl]-4-[4-(2-methoxynaphthalen-1-yl)butyl]piperazine as an oil.

(2) 0.10 g of 1-[2-(4-Carbamoylphenyl)-2-(4-isopropylpiperazino)ethyl]-4-[4-(2-methoxynaphthalen-1-yl)butyl]piperazine was dissolved in 4 ml of methanol, and 1 ml of 4M hydrogen chloride/ethyl acetate solution was added. The solution was concentrated under reduced pressure, and the resulting solid was washed with ethyl acetate to give 0.10 g of 1-[2-(4-carbamoylphenyl)-2-(4-isopropylpiperazino)ethyl]-4-[4-(2-methoxynaphthalen-1-yl)butyl]piperazine tetrahydrochloride.

The structures and physical property data of the present compound and the compounds prepared similarly are shown in Table 1.

EXAMPLE 10

Synthesis of 1-[2-(3-carbamoylphenyl)-2-(4-isopropylpiperazino)ethyl]-4-[4-(2-methoxynaphthalen-1-yl)butyl]piperazine Tetrahydrochoride (Compound 76 in Table 1)

(1) 0.20 g of 1-[2-(3-Cyanophenyl)-2-(4-isopropylpiperazino)ethyl]-4-[4-(2-methoxynaphthalen-1-yl)butyl]piperazine obtained by the procedure similar to that of Example 2 was dissolved in 2 ml of t-butanol, and 70 mg of potassium hydroxide was added, followed by reflux with heating for 2 hours. The reaction solution was cooled to room temperature, diluted with chloroform and washed with a saturated aqueous sodium bicarbonate solution and a saturated aqueous sodium chloride solution. The organic layer was dried over anhydrous sodium sulfate. After removal of the drying agent by filtration, the filtrate was concentrated under reduced pressure. The residue was purified by a silica gel column chromatography (Chromatorex NH, hexane:ethyl acetate=2:1) to give 74 mg of 1-[2-(3-carbamoylphenyl)-2-(4-isopropylpiperazino)ethyl]-4-[4-(2-methoxynaphthalen-1-yl)butyl]piperazine as an oil.

(2) 74 mg of 1-[2-(3-Carbamoylphenyl)-2-(4-isopropylpiperazino)ethyl]-4-[4-(2-methoxynaphthalen-1-yl)butyl]piperazine was dissolved in 4 ml of methanol, and 1 ml of 4M hydrogen chloride/ethyl acetate solution was added. The solution was concentrated under reduced pressure, and the resulting solid was washed with ethyl acetate to give 70 mg of 1-[2-(3-carbamoylphenyl)-2-(4-isopropylpiperazino)ethyl]-4-[4-(2-methoxynaphthalen-1-yl)butyl]piperazine tetrahydrochloride.

The structures and physical property data of the present compound and the compounds prepared similarly are shown in Table 1.

EXAMPLE 11

Synthesis of 1-[2-(4-fluorophenyl)-2-piperidin-4-yl-ethyl]-4-[4-(2-methoxynaphthalen-1-yl)butyl]piperazine (Compound 81 in Table 2)

(1) 48.3 ml of Diisopropylamine was dissolved in 200 ml of tetrahydrofuran, and 137 ml of 2.5 M n-butyl lithium/hexane solution was added dropwise with ice-cooling. To the reaction solution was added dropwise a 100 ml of tetrahydrofuran solution of 25.2 g of p-fluorophenylacetic acid, 28.4 ml of hexamethylphosphoric triamide (HMPA) was added, and the temperature was elevated to room temperature, followed by stirring for 30 minutes. After ice-cooling, to the reaction solution was added dropwise 100 ml of a tetrahydrofuran solution of 32.5 g of 1-t-butoxycarobnyl-4-piperidone, and the temperature was elevated to room temperature, followed by stirring for 3 hours. To the reaction solution was added dropwise water and, after extraction with ethyl acetate, the aqueous layer was made acidic with potassium hydrogensulfate, and extracted with ethyl acetate. The organic layer was washed with a saturated aqueous sodium chloride solution and dried over anhydrous sodium sulfate. After removal of the drying agent by filtration, the filtrate was concentrated under reduced pressure. To the residue was added ether, followed by stirring at room temperature. The precipitated crystals were collected by filtration and washed with ether to give 30.0 g of 1-t-butoxycarbonyl-4-[carboxy-(4-fluorophenyl) methyl]-4-hydroxypiperidine as a powder.

(2) 20.0 g of 1-t-Butoxycarbonyl-4-[carboxy-(4-fluorophenyl)methyl]-4-hydroxypiperidine was suspended in 40 ml of chloroform, and 40 ml of conc. sulfuric acid was added dropwise with ice-cooling. The reaction solution was refluxed with heating for 3 hours and, after ice-cooling, 250 ml of 4M sodium hydroxide solution, 200 ml of 1,4-dioxane and 14.8 g of di-t-butyldicarbonate were added. After stirring at room temperature for 30 minutes, the reaction solution was made acidic with potassium hydrogensulfate, followed by extraction with chloroform. The organic layer was washed with a saturated aqueous sodium chloride solution and dried over anhydrous sodium sulfate. After removal of the drying agent by filtration, the filtrate was concentrated under reduced pressure. The residue was purified by a silica gel column chromatography (Wako-gel C-200, chloroform:methanol=10:1) to give 18.0 g of 1-t-butoxycarbonyl-4-[carboxy-(4-fluorophenyl)methyl]-3,6-dihydro-2H-pyridine as an oil.

(3) 5.0 g of 1-t-Butoxycarbonyl-4-[carboxy-(4-fluorophenyl)methyl]-3,6-dihydro-2H-pyridine was dissolved in 50 ml of methanol, and 0.50 g of palladium hydroxide/carbon was added, followed by stirring under a hydrogen atmosphere at room temperature for 2 days. After removal of the catalyst by Celite filtration, the filtrate was concentrated under reduced pressure to give 3.6 g of a crude 1-t-butoxycarbonyl-4-[carboxy-(4-fluorophenyl)methyl] piperidine.

(4) 2.2 g of 1-t-Butoxycarbonyl-4-[carboxy-(4-fluorophenyl)methyl]piperidine was dissolved in 20 ml of dimethylformamide, and 2.0 g of 1-[4-(2-methoxynaphthalen-1-yl)butyl]piperazine dihydrochloride, 1.9 g of 1-(3,3-dimethylaminopropyl)-3-ethylcarbodiimide hydrochloride, 1.9 g of 1-hydroxybenzotriazole monohydrate and 3.5 ml of triethylamine were added, followed by stirring at room temperature overnight. The reaction solution was diluted with ethyl acetate and washed with a saturated aqueous sodium bicarbonate solution and a saturated aqueous sodium chloride solution. The organic layer was dried over anhydrous sodium sulfate. After removal of the drying agent by filtration, the filtrate was concentrated under reduced pressure. The residue was purified by a silica gel column chromatography (Chromatorex NH, hexane:ethyl acetate=3:1) to give 2.4 g of 1-t-butoxycarbonyl-4-(1-(4-fluorophenyl)-2-{4-[4-(2-methoxynaphthalen-1-yl)butyl] piperazin-1-yl}-2-oxoethyl)piperidine as an oil.

(5) 2.1 g of 1-t-Butoxycarbonyl-4-(1-(4-fluorophenyl)-2-{4-[4-(2-methoxynaphthalen-1-yl)butyl]piperazin-1-yl}-2-oxoethyl)piperidine was dissolved in 10 ml of methanol, and 10 ml of 4M hydrogen chloride/1,4-dioxane solution was added, followed by stirring at room temperature for 2 hours. After concentration of the reaction solution under reduced pressure, to the residue was added ether, followed by stirring at room temperature. The precipitated crystals were filtered and washed with ether to give 1.7 g of 4-(1-(4-fluorophenyl)-2-{4-[4-(2-methoxynaphthalen-1-yl)butyl] piperazin-1-yl}-2-oxoethyl)piperidine dihydrochloride.

(6) 0.15 g of 4-(1-(4-Fluorophenyl)-2-{4-[4-(2-methoxynaphthalen-1-yl)butyl]piperazin-1-yl}-2-oxoethyl) piperidine dihydrochloride was dissolved in 1M aqueous sodium hydroxide solution and extracted with chloroform. The organic layer was dried over anhydrous sodium sulfate. After removal of the drying agent by filtration, the filtrate was concentrated under reduced pressure. The residue was dissolved in 5 ml of tetrahydrofuran, and 10 mg lithium aluminum hydride was added, followed by stirring at 50° C. for 15 minutes. The reaction solution was cooled to room temperature and diluted with ether, and 25% aqueous ammonia solution was added dropwise. The precipitate was removed by Celite filtration, the filtrate was concentrated under reduced pressure, and the residue was purified by a silica gel column chromatography (Chromatorex NH, hexane:ethyl acetate=4:1) to give 0.13 g of 1-[2-(4-fluorophenyl)-2-piperidin-4-yl-ethyl]-4-[4-(2-methoxynaphthalen-1-yl)butyl]piperazine as an oil.

The structures and physical property data of the present compound and the compounds prepared similarly are shown in Table 2.

EXAMPLE 12

Synthesis of 4-{1-(4-fluorophenyl)-2-[4-(naphthalen-1-yl-butyl)piperazin-1-yl]ethyl}-1-methylpiperidin-4-ol trihydrochloride (Compound 83 in Table 2)

(1) 2.37 g of 1-t-Butoxycarbonyl-4-[carboxy-(4-fluorophenyl)methyl]-4-hydroxypiperidine obtained in Example 11(1) was dissolved in 20 ml of dimethylformamide, and 2.50 g of 1-(4-naphthalen-1-yl-butyl)piperazine dihydrochloride, 1.9 g of 1-(3,3-dimethylaminopropyl)-3-ethylcarbodiimide hydrochloride, 1.9 g of 1-hydroxybenzotriazole monohydrate and 3.5 ml of triethylamine were added, followed by stirring at room temperature overnight. The reaction solution was diluted with ethyl acetate and washed with a saturated aqueous sodium bicarbonate solution and a saturated aqueous sodium chloride solution. The organic layer was dried over anhydrous sodium sulfate. After removal of the drying agent by filtration, the filtrate was concentrated under reduced pressure. The residue was purified by a silica gel column chromatography (Chromatorex NH, hexane:ethyl acetate=3:1) to give 1.96 g of 1-t-butoxycarbonyl-4-{1-(4-fluorophenyl)-2-[4-(naphthalen-1-yl-butyl)piperazin-1-yl]-2-oxoethyl}-4-hydroxypiperidine as an oil.

(2) 1.04 g of 1-t-Butoxycarbonyl-4-{1-(4-fluorophenyl)-2-[4-(naphthalen-1-yl-butyl)piperazin-1-yl]-2-oxoethyl}-4-hydroxypiperidine was dissolved in 10 ml of methanol, and 20 ml of 4M hydrogen chloride/1,4-dioxane solution was added, followed by stirring at room temperature for 2 hours. The reaction solution was concentrated under reduced pressure, ethyl acetate was added to the residue, and the mixture was washed with 1M aqueous sodium hydroxide solution and a saturated aqueous sodium solution. The organic layer was dried over anhydrous sodium sulfate. After removal of the drying agent by filtration, the filtrate was concentrated under reduced pressure. The residue was dissolved in 9 ml of acetonitrile, and 640 μl of 37% formalin, 190 μl of acetic acid and 160 mg of sodium cyanoborohydride were added, followed by stirring at room temperature for an hour. The reaction solution was diluted with ethyl acetate and washed with a saturated aqueous sodium bicarbonate solution and a saturated aqueous sodium chloride solution. The organic layer was dried over anhydrous sodium sulfate. After removal of the drying agent by filtration, the filtrate was concentrated under reduced pressure. The residue was purified by a silica gel column chromatography (Chromatorex NH, hexane:ethyl acetate=2:1) to give 0.44 g of 4-{1-(4-fluorophenyl)-2-[4-(naphthalen-1-yl-butyl)piperazin-1-yl]-2-oxoethyl}-1-methylpiperidin-4-ol as an oil.

(3) 0.25 g of 4-{1-(4-Fluorophenyl)-2-[4-(naphthalen-1-yl-butyl)piperazin-1-yl]-2-oxoethyl}-1-methylpiperidin-4- ol was dissolved in 3 ml of tetrahydrofuran, and 18 mg of lithium aluminum hydride was added, followed by stirring at 50° C. for 15 minutes. The reaction solution was cooled to room temperature and diluted with ether, and 25% aqueous ammonia solution was added dropwise. The precipitate was removed by Celite filtration, the filtrate was concentrated under reduced pressure, and the residue was purified by a silica gel column chromatography (Chromatorex NH, hexane:ethyl acetate=4:1) to give 33 mg of 4-{1-(4-fluorophenyl)-2-[4-(naphthalen-1-yl-butyl)piperazin-1-yl]ethyl}-1-methylpiperidin-4-ol as an oil.

(4) 33 mg of 4-{1-(4-Fluorophenyl)-2-[4-(naphthalen-1-yl-butyl)piperazin-1-yl]ethyl}-1-methylpiperidin-4-ol was dissolved in 4 ml of methanol, and 1 ml of 4M hydrogen chloride/ethyl acetate solution was added. The solution was concentrated under reduced pressure, and the resulting solid was washed with ethyl acetate to give 35 mg of 4-{(1-(4-fluorophenyl)-2-[4-(naphthalen-1-yl-butyl)piperazin-1-yl]ethyl}-1-methylpiperidin-4-ol trihydrochloride.

The structures and physical property data of the present compound and the compounds prepared similarly are shown in Table 2.

EXAMPLE 13

Synthesis of 1-[2-(4-fluorophenyl)-2-(1-methyl-1,2,3,6-tetrahydropyridin-4-yl)ethyl]-4-(4-naphthalen-1-yl-butyl)piperazine (Compound 84 in Table 2)

(1) 0.49 g of 1-t-Butoxycarbonyl-4-[carboxy-(4-fluorophenyl)methyl]-3,6-dihydro-2H-pyridine obtained in Example 11(2) was dissolved in 5 ml of dimethylformamide, and 0.55 g of 1-(4-naphthalen-1-yl-butyl)piperazine dihydrochloride, 0.34 g of 1-(3,3-dimethylaminopropyl)-3-ethylcarbodiimide hydrochloride, 0.34 g of 1-hydroxybenzotriazole monohydrate and 0.5 ml of triethylamine were added, followed by stirring at room temperature overnight. The reaction solution was diluted with ethyl acetate and washed with a saturated aqueous sodium bicarbonate solution and a saturated aqueous sodium chloride solution. The organic layer was dried over anhydrous sodium sulfate. After removal of the drying agent by filtration, the filtrate was concentrated under reduced pressure. The residue was purified by a silica gel column chromatography (Chromatorex NH, hexane:ethyl acetate=2:1) to give 0.53 g of 1-t-butoxycarbonyl-4-{1-(4-fluorophenyl)-2-[4-(4-naphthalen-1-yl-butyl)piperazin-1-yl]-2-oxoethyl}-3,6-dihydro-2H-pyridine as an oil.

(2) 0.49 g of 1-t-Butoxycarbonyl-4-{1-(4-fluorophenyl)-2-[4-(4-naphthalen-1-yl-butyl)piperazin-1-yl]-2-oxoethyl}-3,6-dihydro-2H-pyridine was dissolved in 5 ml of methanol, and 20 ml of 4M hydrogen chloride/1,4-dioxane solution was added, followed by stirring at room temperature for 2 hours. The reaction solution was concentrated under reduced pressure, ethyl acetate was added to the residue, the mixture was washed with 1M aqueous sodium hydroxide solution and a saturated aqueous sodium solution. The organic layer was dried over anhydrous sodium sulfate. After removal of the drying agent by filtration, the filtrate was concentrated under reduced pressure. The residue was dissolved in 5 ml of acetonitrile, and 340 µl of 37% formalin, 200 µl of acetic acid and 90 mg of sodium cyanoborohydride were added, followed by stirring at room temperature for an hour. The reaction solution was diluted with ethyl acetate and washed with a saturated aqueous sodium bicarbonate solution and a saturated aqueous sodium chloride solution. The organic layer was dried over anhydrous sodium sulfate. After removal of the drying agent by filtration, the filtrate was concentrated under reduced pressure. The residue was purified by a silica gel column chromatography (Chromatorex NH, hexane:ethyl acetate=2:1) to give 0.25 g of 4-{1-(4-fluorophenyl)-2-[4-(4-naphthalen-1-yl-butyl)piperazin-1-yl]-2-oxoethyl}-1-methyl-3,6-dihydro-2H-pyridine as an oil.

(3) 0.25 g of 4-{1-(4-Fluorophenyl)-2-[4-(4-naphthalen-1-yl-butyl)piperazin-1-yl]-2-oxoethyl}-1-methyl-3,6-dihydro-2H-pyridine was dissolved in 3 ml of tetrahydrofuran, and 18 mg of lithium aluminum hydride was added, followed by stirring at 50° C. for 15 minutes. The reaction solution was cooled to room temperature and diluted with ether, and 25% aqueous ammonia solution was added dropwise. The precipitate was removed by Celite filtration, the filtrate was concentrated under reduced pressure, and the residue was purified by a silica gel column chromatography (Chromatorex NH, hexane:ethyl acetate=4:1) to give 0.10 g of 1-[2-(4-fluorophenyl)-2-(1-methyl-1,2,3,6-tetrahydropyridin-4-yl)ethyl]-4-(4-naphthalen-1-yl-butyl)piperazine as an oil.

The structures and physical property data of the present compound and the compounds prepared similarly are shown in Table 2.

EXAMPLE 14

Synthesis of 1-[2-(4-fluorophenyl)-2-(1-isopropylpiperidin-4-yl)ethyl]-4-[4-(2-methoxynaphthalen-1-yl)butyl]piperazine trihydrochloride (Compound 82 in Table 2)

(1) 0.20 g of 4-(1-(4-Fluorophenyl)-2-{4-[4-(2-methoxynaphthalen-1-yl)butyl]piperazin-1-yl}-2-oxoethyl)piperidine hydrochloride obtained in Example 11(5) was dissolved in 2 ml of dimethylformamide, and 93 mg of potassium carbonate and 41 µl of 2-iodopropane were added, followed by stirring at room temperature overnight. The reaction solution was diluted with ethyl acetate and washed with a saturated aqueous sodium bicarbonate solution and a saturated aqueous sodium chloride solution. The organic layer was dried over anhydrous sodium sulfate. After removal of the drying agent by filtration, the filtrate was concentrated under reduced pressure. The residue was purified by a silica gel column chromatography (Chromatorex NH, hexane:ethyl acetate=4:1) to give 0.15 g of 1-isopropyl-4-(1-(4-fluorophenyl)-2-{4-[4-(2-methoxynaphthalen-1-yl)butyl]piperazin-1-yl}-2-oxoethyl)piperidine as an oil.

(2) 0.14 g of 1-Isopropyl-4-(1-(4-fluorophenyl)-2-{4-[4-(2-methoxynaphthalen-1-yl)butyl]piperazin-1-yl}-2-oxoethyl)piperidine was dissolved in 5 ml of tetrahydrofuran, and 10 ml of lithium aluminum hydride was added, followed stirring at 50° C. for 15 minutes. The reaction solution was cooled to room temperature and diluted with ether, and 25% aqueous ammonia solution was added dropwise. The precipitate was removed by Celite filtration, the filtrate was concentrated under reduced pressure, and the residue was purified by a silica gel column chromatography (Chromatorex NH, hexane:ethyl acetate= 4:1) to give 0.13 g of 1-[2-(4-fluorophenyl)-2-(1-isopropylpiperidin-4-yl)ethyl]-4-[4-(2-methoxynaphthalen-1-yl)butyl]piperazine as an oil.

(3) 0.11 g of 1-[2-(4-Fluorophenyl)-2-(1-isopropylpiperidin-4-yl)ethyl]-4-[4-(2-methoxynaphthalen-1-yl)butyl]piperazine was dissolved in 4 ml of methanol, and 1 ml of 4M hydrogen chloride/ethyl acetate solution was added. The solution was concentrated under reduced pressure, and the resulting solid was washed with ethyl acetate to give 0.12 g of 1-[2-(4-fluorophenyl)-2-(1-isopropylpiperidin-4-yl)ethyl]-4-[4-(2-methoxynaphthalen-1-yl)butyl]-piperazine trihydrochloride.

The structures and physical property data of the present compound and the compounds prepared similarly are shown in Table 2.

EXAMPLE 15

Synthesis of 1-[2-(4-fluorophenyl)-2-(4-methylpiperazino)ethyl]-4-[4-naphthalen-1-yl-butyl] piperazine hydrochloride (Optically Active Compound)

1-[2-(4-Fluorophenyl)-2-(4-methylpiperazino)ethyl]-4-[4-naphthalen-1-yl-butyl]piperazine hydrochloride obtained in Example 2 (6) was resolved by means of HPLC (Chiralpak AD (manufactured by Daicel Co.), 2φ×25 cm, mobile phase: hexane-isopropanol-diethylamine=95:5:0.1, flow rate 5.0 ml/min). After the resolution, the solvent was concentrated under reduced pressure, dissolved in ethanol, and introduced to the hydrochloride by 4M hydrogen chloride/ethyl acetate solution, and the solvent was concentrated under reduced pressure to give 1-[2-(4-fluorophenyl)-2-(4-methylpiperazino)ethyl]-4-[4-naphthalen-1-yl-butyl] piperazine hydrochloride (optically active compound).

(+)-1-[2-(4-Fluorophenyl)-2-(4-methylpiperazino)ethyl]-4-[4-naphthalen-1-yl-butyl]piperazine hydrochloride $[\alpha]_D^{25}$=+15.8 (c=0.24, MeOH), Retention time; 7.0 minutes.

m.p. 193–195° C. (ethanol)

(−)-1-[2-(4-Fluorophenyl)-2-(4-methylpiperazino)ethyl]-4-[4-naphthalen-1-yl-butyl]piperazine hydrochloride $[\alpha]_D^{25}$=−15.0 (c=0.24, MeOH), Retention time; 10.9 minutes. m.p. 193–195° C. (ethanol)

The structures and physical property data of the present compound and the compounds prepared similarly are shown in Table 1.

EXAMPLE 16

Synthesis of (+)-1-[2-(4-fluorophenyl)-2-(4-isopropylpiperazino)ethyl]-4-[4-(2-methoxynaphthalen-1-yl)butyl]piperazine tetrahydrochloride (Compound 61 in Table 1)

(1) 1.0 g of 2-Chloro-4'-fluoroacetophenone was dissolved in 5 ml of tetrahydrofuran, and 0.16 g of (S)-5,5-diphenyl-2-methyl-3,4-propano-1,3,2-oxazaborolidine and 1M borane-tetrahydrofuran complex 7.0 ml of tetrahydrofuran solution were added with ice-cooling, followed by stirring for 10 minutes. Then, to the reaction solution was added 2 ml of 4M aqueous sodium hydroxide solution, followed by stirring at room temperature for 4 hours. The reaction solution was concentrated under reduced pressure, and the residue was dissolved in ether and washed with a saturated aqueous sodium bicarbonate solution and a saturated aqueous sodium chloride solution. The organic layer was dried over anhydrous sodium sulfate. After removal of the drying agent by filtration, the filtrate was concentrated under reduced pressure. The residue was purified by a silica gel column chromatography (Wako-gel C200, hexane:ethyl acetate=10:1) to give an optically active 2-(4-fluorophenyl) oxirane (0.85 g) as an oil.

(2) 0.80 g of the optically active form of 2-(4-fluorophenyl)oxirane was dissolved in ethanol, and 3.2 g of 1-[4-(2-methoxynaphthalen-1-yl)butyl]piperazine was added, followed by reflux with heating or 2 hours. The reaction solution was cooled to room temperature and concentrated under reduced pressure. The residue was dissolved in chloroform and washed with a saturated aqueous sodium bicarbonate solution and a saturated aqueous sodium chloride solution. The organic layer was dried over anhydrous sodium sulfate. After removal of the drying agent by filtration, the filtrate was concentrated under reduced pressure. The residue was purified by silica gel column chromatography (Chromatorex NH, hexane:ethyl acetate=2:1) to give 1.2 g of optically active 1-[2-hydroxy-2-(4-fluorophenyl)ethyl]-4-[4-(2-methoxynaphthalen-1-yl)butyl] piperazin as a solid.

(3) The optically active 0.12 g of 1-[2-hydroxy-2-(4-fluorophenyl)ethyl]-4-[4-(2-methoxynaphthalen-1-yl)butyl] piperazine and 0.15 ml of triethylamine were dissolved in 5 ml of methylene chloride and, after ice-cooling, 43 μl of methanesulfonyl chloride was added, followed by stirring at room temperature for 30 minutes. To the reaction solution were added 0.15 ml of triethylamine and 0.11 g of 1-isopropylpiperazine dihydrochloride, successively, followed by stirring at room temperature for 3 hours. The reaction solution was concentrated under reduced pressure, and the residue was dissolved in ethyl acetate and washed with a saturated aqueous sodium bicarbonate solution and a saturated aqueous sodium chloride solution. The organic layer was dried over anhydrous sodium sulfate. After removal of the drying agent by filtration, the filtrate was concentrated under reduced pressure. The residue was purified by a silica gel column chromatography (Chromatorex NH, hexane:ethyl acetate=4:1) to give 0.12 g of (+)-1-[2-(4-fluorophenyl)-2-(4-isopropylpiperazino)ethyl]-4-[4-(2-methoxynaphthalen-1-yl)butyl]piperazine.

(4) 0.12 g of (+)-1-[2-(4-Fluorophenyl)-2-(4-isopropylpiperazino)ethyl]-4-[4-(2-methoxynaphthalen-1-yl)butyl]piperazine was dissolved in 4 ml of methanol, and 1 ml of 4M hydrogen chloride/ethyl acetate solution was added. After concentration under reduced pressure, the resulting solid was washed with ethyl acetate to give 0.12 g of (+)-1-[2-(4-fluorophenyl)-2-(4-isopropylpiperazino) ethyl]-4-[4-(2-methoxynaphthalen-1-yl)butyl]piperazine tetrahydrochloride.

The structures and physical property data of the present compound and the compounds prepared similarly are shown in Table 1.

EXAMPLE 17

Synthesis of (−)-1-[2-(4-fluorophenyl)-2-(4-isopropylpiperazino)ethyl]-4-[4-(2-methoxynaphthalen-1-yl)butyl]piperazine tetrahydrochloride (Compound 62 in Table 1)

Following a procedure similar to that of Example 16 using (R)-5,5-diphenyl-2-methyl-3,4-propano-1,3,2-oxazaborolidine, thereby there was obtained 0.12 g of (−)-1-[2-(4-fluorophenyl)-2-(4-isopropylpiperazino)ethyl]-4-[4-(2-methoxynaphthalen-1-yl)butyl]piperazine tetrahydrochloride.

The structures and physical property data of the present compound and the compounds prepared similarly are shown in Table 1.

TABLE 1[*1]

$$R^1-N\underset{\underset{N-(CH_2)_n-Ar^2}{|}}{\overset{Ar^1}{N}}$$

| Compound No. | Example No. | Ar[1] | Ar[2] | R[1] | n | M.P.[*2] (° C.) | Solvent for recrystalization |
|---|---|---|---|---|---|---|---|
| 1 | 2 | 4-F—Ph | 1-Naph | Me | 1 | 173–175 | Ether |
| 2 | 2 | 4-F—Ph | 1-Naph | Me | 2 | 174–176 | EtOH |
| 3 | 2 | 4-F—Ph | 1-Naph | Me | 3 | 175–177 | EtOH |
| 4 | 2 | 4-F—Ph | 1-Naph | Me | 4 | 193–195[*3] | AcOEt |
| 5[*10] | 15 | 4-F—Ph | 1-Naph | Me | 4 | 193–195[*3] | EtOH |
| 6[*11] | 15 | 4-F—Ph | 1-Naph | Me | 4 | 193–195[*3] | EtOH |
| 7 | 2 | 4-F—Ph | 1-Naph | Me | 5 | 170–172 | EtOH |
| 8 | 2 | 4-F—Ph | 1-Naph | Me | 6 | 182–184 | EtOH |
| 9 | 2 | 4-F—Ph | 2-Naph | Me | 1 | 189–191 | EtOH-Ether |
| 10 | 2 | 4-F—Ph | 2-Naph | Me | 2 | 187–189 | EtOH |
| 11 | 2 | 4-F—Ph | 2-Naph | Me | 3 | 180–182 | EtOH |
| 12 | 2 | 4-F—Ph | 2-Naph | Me | 4 | 185–187 | EtOH |
| 13 | 1 | 4-F—Ph | 1-Naph | H | 4 | 180–182[*3] | MeOH |
| 14 | 3 | 4-F—Ph | 1-Naph | Et | 4 | 120–122 | EtOH |
| 15 | 3 | 4-F—Ph | 1-Naph | Pr | 4 | 150–152 | EtOH |
| 16 | 3 | 4-F—Ph | 1-Naph | iPr | 4 | 127–129 | EtOH |
| 17 | 1 | 4-F—Ph | 1-Naph | cPr | 4 | 161–163 | EtOH |
| 18 | 1 | 4-F—Ph | 1-Naph | cHex | 4 | 171–173 | EtOH |
| 19 | 1 | 4-F—Ph | 1-Naph | Ph | 4 | 172–174 | EtOH-Ether |
| 20 | 4 | 4-F—Ph | 1-Naph | Amidyl | 4 | 171–173 | EtOH |
| 21 | 1 | 4-F—Ph | 1-Naph | Pyrimidin-2-yl | 4 | 190–192 | EtOH-Ether |
| 22 | 2 | 1-Naph | 1-Naph | Me | 4 | 171–173 | EtOH |
| 23 | 2 | 1-Naph | 2-Naph | Me | 4 | 80–83 | EtOH |
| 24 | 2 | 2-Naph | 1-Naph | Me | 4 | 122–124 | EtOH |
| 25 | 2 | 2-Naph | 2-Naph | Me | 4 | 133–135 | EtOH |
| 26 | 1 | Ph | 1-Naph | Me | 4 | 167–169 | EtOH |
| 27 | 1 | 3-F—Ph | 1-Naph | Me | 4 | 173–175 | EtOH |
| 28 | 1 | 4-Cl—Ph | 1-Naph | Me | 4 | 175–177 | EtOH |
| 29 | 1 | 4-Me—Ph | 1-Naph | Me | 4 | 186–188 | EtOH |
| 30 | 1 | 2-MeO—Ph | 1-Naph | Me | 4 | 114–116 | EtOH |
| 31 | 1 | 3-MeO—Ph | 1-Naph | Me | 4 | 123–125 | EtOH |
| 32 | 1 | 4-MeO—Ph | 1-Naph | Me | 4 | 138–140 | EtOH |
| 33 | 1 | 2-Br—Ph | 1-Naph | Me | 4 | amorphous[*4] | |
| 34 | 1 | 3-Br—Ph | 1-Naph | Me | 4 | 119–121 | EtOH |
| 35 | 1 | 4-Br—Ph | 1-Naph | Me | 4 | 168–170 | EtOH |
| 36 | 1 | 4-Biphenyl | 1-Naph | Me | 4 | 123–125 | EtOH |
| 37 | 1 | 4-CF$_3$—Ph | 1-Naph | Me | 4 | 128–130 | EtOH |
| 38 | 1 | 4-NO$_2$—Ph | 1-Naph | Me | 4 | 176–178 | EtOH |
| 39 | 5 | 4-NH$_2$—Ph | 1-Naph | Me | 4 | 152–154 | EtOH |
| 40 | 1 | 4-BnO—Ph | 1-Naph | Me | 4 | 151–153 | EtOH |
| 41 | 2 | 4-F—Ph | 4-Quinolyl | Me | 4 | 159–161 | EtOH |
| 42 | 2 | 4-F—Ph | 4-Me$_2$N-1-Naph | Me | 4 | 173–175 | EtOH |
| 43 | 2 | 4-F—Ph | Benzo[b]furan-3-yl | Me | 4 | 174–176 | EtOH |
| 44 | 2 | 4-F—Ph | Indole-3-yl | Me | 4 | 163–165 | EtOH |
| 45 | 2 | 4-F—Ph | 4-Cl-Benzothiophen-3-yl | Me | 4 | 174–176 | EtOH |
| 46 | 6 | 4-F—Ph | 6-F-1,2-Benzisoxazole-3-yl | Me | 4 | 170–173 | EtOH |
| 47 | 2 | 4-F—Ph | 4-Methoxy-6H-dibenzo[b,d]pyran-1-yl | iPr | 3 | 93–95 | EtOH |
| 48 | 2 | 4-F—Ph | 4-Methoxy-6H-dibenzo[b,d]pyran-1-yl | iPr | 4 | 103–105 | EtOH |
| 49 | 1 | 4-F—Ph | 4-Me$_2$N-1-Naph | iPr | 4 | 122–124 | EtOH |
| 50 | 2 | 4-F—Ph | 4-MeO-1-Naph | Me | 4 | 178–181 | EtOH |
| 51 | 2 | 4-F—Ph | 2-MeO-1-Naph | Me | 4 | 173–175 | EtOH |
| 52 | 2 | 4-F—Ph | 4-Me-1-Naph | Me | 4 | 180–182 | EtOH |
| 53 | 2 | 4-F—Ph | 4-F-1-Naph | Me | 4 | 174–176 | EtOH |
| 54 | 2 | 4-F—Ph | 2-MeO-1-Naph | iPr | 4 | 154–156 | EtOH |

TABLE 1[*1]-continued $$R^1-N\underset{\underset{}{}}{\overset{}{\bigcirc}}N-\overset{Ar^1}{\underset{}{CH}}-CH_2-N\underset{}{\overset{}{\bigcirc}}N-(CH_2)_n-Ar^2$$

| Compound No. | Example No. | Ar[1] | Ar[2] | R[1] | n | M.P.[*2] (° C.) | Solvent for recrystalization |
|---|---|---|---|---|---|---|---|
| 55 | 7 | 4-F—Ph | 2-OH-1-Naph | iPr | 4 | amorphous[*5] | |
| 56 | 8 | 4-F—Ph | 2-iPrO-1-Naph | iPr | 4 | 167–169 | EtOH |
| 57 | 8 | 4-F—Ph | 2-EtO-1-Naph | iPr | 4 | amorphous[*6] | |
| 58 | 1 | 4-F—Ph | 2-MeO-1-Naph | Cycropentyl | 4 | 163–164 | EtOH |
| 59 | 1 | 4-F—Ph | 2-MeO-1-Naph | 1-Ethylpropyl | 4 | 141–143 | EtOH |
| 60 | 1 | 4-F—Ph | 2-MeO-1-Naph | Allyl | 4 | 138–140 | EtOH |
| 61[*12] | 15, 16 | 4-F—Ph | 2-MeO-1-Naph | iPr | 4 | 183–185[*3] | AcOEt[*20] |
| 62[*13] | 15, 17 | 4-F—Ph | 2-MeO-1-Naph | iPr | 4 | 183–185[*3] | AcOEt[*20] |
| 63 | 15 | 4-F—Ph | 2-MeO-1-Naph | tBu | 4 | 116–118 | EtOH |
| 64[*14] | 15 | 4-F—Ph | 2-MeO-1-Naph | Me | 4 | 206–209[*3] | AcOEt[*20] |
| 65[*15] | 15 | 4-F—Ph | 2-MeO-1-Naph | Me | 4 | 206–209[*3] | AcOEt[*20] |
| 66 | 1 | 4-F—Ph | 2-MeO-1-Naph | H | 4 | 167–169[*3] | AcOEt[*20] |
| 67[*16] | 15 | 4-F—Ph | 2-MeO-1-Naph | H | 4 | 167–169[*3] | AcOEt[*20] |
| 68[*17] | 15 | 4-F—Ph | 2-MeO-1-Naph | H | 4 | 167–169[*3] | AcOEt[*20] |
| 69[*18] | 15 | 4-F—Ph | 2-iPrO-1-Naph | iPr | 4 | 175–177[*3] | AcOEt[*20] |
| 70[*19] | 15 | 4-F—Ph | 2-iPrO-1-Naph | iPr | 4 | 175–177[*3] | AcOEt[*20] |
| 71 | 2 | 4-F—Ph | 4-Methoxy-6H-dibenzo[b,d]pyran-1-yl | iPr | 1 | 197–200[*3] | AcOEt[*20] |
| 72 | 2 | 4-F—Ph | 4-Methoxy-6H-dibenzo[b,d]pyran-1-yl | iPr | 2 | 200–203[*3] | AcOEt[*20] |
| 73 | 6 | 4-F—Ph | 2-Br-1-Naph | iPr | 4 | 147–150 | EtOH |
| 74 | 2 | 3-CN—Ph | 2-MeO-1-Naph | iPr | 4 | 142–144 | EtOH |
| 75 | 9 | 4-CONH$_2$—Ph | 2-MeO-1-Naph | iPr | 4 | 187–189[*3] | AcOEt[*20] |
| 76 | 10 | 3-CONH$_2$—Ph | 2-MeO-1-Naph | iPr | 4 | 185–187[*3] | AcOEt[*20] |
| 77 | 3 | 4-F—Ph | 2-MeO-1-Naph | 1-Cyanoethyl | 4 | amorphous[*7] | |
| 78 | 8 | 4-F—Ph | 2-Methoxycarbonylmethoxy-1-Naph | iPr | 4 | amorphous[*8] | |
| 79 | 8 | 4-F—Ph | 2-Carbamoylmethoxy-1-Naph | iPr | 4 | amorphous[*9] | |

[*1]Notation in Table 1
Ph = Phenyl, Naph = Naphtyl, Me = Methyl, Et = Ethyl, Pr = Propyl, Hex = Hexyl, Bn = Benzyl, iPr = Isopropyl, cPr = Cycropropyl, cHex = Cycrohexyl, tBu = tert-Butyl.
[*2]Maleate unless otherwise noted
[*3]Hydrochloride
[*4]Compound 33 $^1$H-NMR(200MHz, CDCl$_3$)1.6–1.8(m, 4H)2.24(s, 3H)2.3–2.9(m, 20H)3.08(t, 2H, J=7.5Hz)4.12(t, 1H, J=6.0Hz)7.08(m, 1H)7.3–7.6(m, 7H)7.70(m, 1H)7.84(m, 1H)8.04(m, 1H)MS(m/z)549(M+H)551(M+2+H)
[*5]Compound 55 $^1$H-NMR(300MHz, CDCl$_3$)1.00(d, 6H, J=7.5Hz)1.60(m, 2H)1.72(m, 2H)2.4–2.8(m, 20H) 2.94(m, 3H)3.56(t, 1H, J=7.0Hz)6.99(m, 2H)7.1–7.3(m, 4H)7.42(m, 1H)7.60(d, 1H, J=8.0Hz)7.75(d, 1H, J=7.5Hz)7.86(d, 1H, J=7.5Hz). ESIMS(Positive)533(M+H)$^+$
[*6]Compound 57 $^1$H-NMR(300MHz, CDCl$_3$)1.01(d, 6H, J=7.5Hz)1.42(t, 3H, J=7.5Hz)1.61(m, 4H)2.2–2.7(m, 20H)2.82 (m, 1H)3.06(m, 2H)3.54(t, 1H, J=7.0Hz)4.15(q, 2H, J=7.5Hz)6.98(m, 2H)7.16–7.34(m, 4H)7.44(m, 1H)7.66(d, 1H, J=8.0Hz)7.76(d, 1H, J=7.5Hz)7.96(d, 1H, J=7.5Hz). ESIMS (Positive)561(M+H)$^+$
[*7]Compound 77 $^1$H-NMR(300MHz, CDCl$_3$)1.42(m, 3H), 1.50–1.70(m, 6H)2.2–2.9(m, 15H)3.06(m, 2H)3.50–3.64(m, 2H)3.94(s, 3H)7.00(m, 2H)7.20–7.36(m, 4H)7.46(m, 1H)7.70(d, 1H, J=8.0Hz)7.78(d, 1H, J=7.5Hz)7.94(d, 1H, J=7.5Hz). ESIMS (Positive)558(M+H)$^+$
[*8]Compound 78 $^1$H-NMR(300MHz, CDCl$_3$)1.00(d, 6H, J=7.5Hz)1.61(m, 4H)2.3–2.9(m, 21H)3.14(m, 2H)3.54(m, 1H)3.80(s, 3H)4.74(s, 2H)6.98(m, 2H)7.10(d, 2H, J=8.0Hz)7.34(m, 4H)7.36(m, 1H)7.46(m, 1H)7.66(d, 1H, J=8.0Hz) 7.78(d, 1H, J=7.5Hz)7.98(d, 1H, J=7.5Hz). ESIMS(Positive)605(M+H)$^+$
[*9]Compound 79 $^1$H-NMR(300MHz, CDCl$_3$)1.02(d, 6H, J=7.5Hz)1.5–1.7(m, 4H)2.1–2.7(m, 20H)2.86(m, 1H)3.10(m, 2H)3.56(m, 1H)4.60(s, 2H)5.90(brs, 1H)6.76(brs, 1H)6.98(m, 2H)7.1–7.2(m, 3H)7.50(m, 1H)7.70(d, 1H, J=8.0Hz)7.80 (d, 1H, J=7.5Hz)7.98(d, 1H, J=7.5Hz). ESIMS (Positive)590(M+H)$^+$
[*10]Optically active Compound 4 $[\alpha]_D^{25}$ + 15.8 (MeOH, c 0.24)
[*11]Optically active Compound 4 $[\alpha]_D^{25}$ − 15.0 (MeOH, c 0.24)
[*12]Compound 61 $[\alpha]_D^{26}$ + 12.1 (MeOH, c 0.20), ESIMS (Positive) 547 (M + H)$^+$
[*13]Compound 62 $[\alpha]_D^{26}$ − 13.1 (MeOH, c 0.24), ESIMS (Positive) 547 (M + H)$^+$
[*14]Compound 64 $[\alpha]_D^{26}$ + 15.3 (MeOH, c 0.20), ESIMS (Positive) 519 (M + H)$^+$
[*15]Compuond 65 $[\alpha]_D^{26}$ − 16.4 (MeOH, c 0.21), ESIMS (Positive) 519 (M + H)$^+$
[*16]Compound 67 $[\alpha]_D^{26}$ + 12.4 (MeOH, c 0.24), ESIMS (Positive) 505 (M + H)$^+$
[*17]Compound 68 $[\alpha]_D^{26}$ − 12.7 (MeOH, c 0.20), ESIMS (Positive) 505 (M + H)$^+$
[*18]Compound 69 $[\alpha]_D^{27}$ + 12.7 (MeOH, c 0.22), ESIMS (Positive) 575 (M + H)$^+$
[*19]Compound 70 $[\alpha]_D^{26}$ − 13.0 (MeOH, c 0.24), ESIMS (Positive) 575 (M + H)$^+$
[*20]Solvent for crystallization

TABLE 2*[1]

[Structure: R¹-N ring with R², R³ substituents, connected through A-B to a carbon bearing Ar¹ and CH₂ to a piperazine-N-N-(CH₂)ₙ-T¹-Ar²]

| Compound No. | Example No. | Ar¹ | Ar² | R¹ | R² | R³ | A—B | T¹ | n | M.P.*[2] (°C.) | Solvent for recrystalization |
|---|---|---|---|---|---|---|---|---|---|---|---|
| 80 | 14 | 4-F—Ph | 1-Naph | Me | H | H | CH—CH₂ | bond | 4 | 190–193*[3] | AcOEt*[10] |
| 81 | 11 | 4-F—Ph | 2-MeO-1-Naph | H | H | H | CH—CH₂ | bond | 4 | amorphous*[5] | |
| 82 | 14 | 4-F—Ph | 2-MeO-1-Naph | iPr | H | H | CH—CH₂ | bond | 4 | 233–235*[3] | AcOEt*[10] |
| 83 | 12 | 4-F—Ph | 1-Naph | Me | H | H | C(OH)—CH₂ | bond | 4 | 156–160*[3] | AcOEt*[10] |
| 84 | 13 | 4-F—Ph | 1-Naph | Me | H | H | C=CH | bond | 4 | amorphous*[6] | |
| 85 | 13 | 4-F—Ph | 2-MeO-1-Naph | iPr | H | H | C=CH | bond | 4 | amorphous*[7] | |
| 86 | 2 | 4-F—Ph | 1-Naph | Me | H | H | N—CH₂ | O | 2 | 163–165 | EtOH |
| 87 | 6 | 4-F—Ph | 1-Naph | Me | H | H | N—CH₂ | O | 3 | 171–172 | EtOH |
| 88 | 6 | 4-F—Ph | 1-Naph | Me | H | H | N—CH₂ | NH | 3 | 136–137*[4] | EtOH |
| 89 | 6 | 4-F—Ph | 1-Naph | Me | H | H | N—CH₂ | N(Me) | 3 | 167–170 | EtOH |
| 90 | 6 | 4-F—Ph | 2-MeO-1-Naph | iPr | H | H | N—CH₂ | —CH=CH— | 2 | 152–154 | EtOH |
| 91 | 6 | 4-F—Ph | 2-MeO-1-Naph | iPr | H | H | N—CH₂ | —C(=O)— | 3 | 132–134 | EtOH |
| 92 | 1 | 5-F—Ph | 2-MeO-1-Naph | H | Me | Me | N—CH₂ | bond | 4 | amorphous*[8] | |
| 93 | 1 | 6-F—Ph | 2-MeO-1-Naph | Me | Me | Me | N—CH₂ | bond | 4 | amorphous*[9] | |

*[1]Notation in Table 2
Ph = Phenyl, Naph = Naphtyl, Me = Methyl, Et = Ethyl, Pr = Propyl, iPr = Isopropyl, bond = single bond.
*[2]Maleate unless otherwise noted
*[3]Hydrochloride
*[4]Free form
*[5]Compound 81 $^1$H-NMR(300MHz, CDCl$_3$)0.90–1.40(m, 5H)1.50–1.80(m, 4H)2.20–2.82(m, 16H)2.90–3.10(m, 3H)3.92(s, 3H)6.90–7.10(m, 4H)7.24(d, 1H, J=8.0Hz)7.30(t, 1H, J=7.5Hz)7.44(d, 1H, J=7.5Hz)7.70(d, 1H, J=8.0Hz)7.78(d, 1H, J=7.5Hz)7.94 (d, 1H, J=7.5Hz). ESIMS(Positive)504(M+H)$^+$
*[6]Compound 84 $^1$H-NMR(300MHz, DMSO-d6)1.63–1.91(m, 4H)2.68–2.86(m, 3H)2.94–3.90(m, 14H)3.91–4.18(m, 2H)6.00(brs, 1H)7.16–7.25(m, 2H)7.33–7.46(m, 4H)7.49–7.59(m, 2H)7.79(d, 1H, J=7.5Hz)7.92(m, 1H)8.08(d, 1H, J=7.5Hz). ESIMS(Positive) 486(M+H)$^+$
*[7]Compound 85 $^1$H-NMR(300MHz, CDCl$_3$)1.04(d, 6H, J=7.5Hz)1.60(m, 4H)2.00(m, 2H)2.20–2.82(m, 12H)3.08(m, 4H)3.42(m, 1H)3.92(s, 3H)5.52(brs, 1H)6.96(m, 2H)7.10–7.36(m, 4H)7.46(m, 1H)7.70(d, 1H, J=8.0Hz)7.78(d, 1H, J=7.5Hz)7.96(d, 1H, J=7.5Hz). ESIMS(Positive)544(M+H)$^+$
*[8]Compound 92 $^1$H-NMR(300MHz, CDCl$_3$)0.90–1.05(m, 6H)1.40–1.70(m, 8H)2.20–2.70(m, 11H)2.75–3.00(m, 4H)3.06(m, 2H)3.60(m, 1H)3.92(s, 3H)7.00(m, 2H)7.16–7.26(m, 4H)7.44(m, 1H)7.70(d, 1H, J=8.0Hz)7.78(d, 1H, J=7.5Hz)7.94(d, 1H, J=7.5Hz). ESIMS(Positive)533(M+H)$^+$
*[9]Compound 93 $^1$H-NMR(300MHz, CDCl$_3$)0.98(d, 3H, J=7.5Hz)1.04(d, 3H, J=7.5Hz)1.60(m, 4H)1.80(m, 2H)1.98(m, 2H)2.10–2.66(m, 17H)2.80–2.90(m, 2H)3.08(m, 2H)3.50(m, 1H)3.92(s, 3H)6.98(m, 2H)7.16–7.34(m, 4H)7.44(m, 1H)7.70(d, 1H, J=8.0Hz)7.78(d, 1H, J=7.5Hz)7.94(d, 1H, J=7.5Hz). ESIMS(Positive)547(M+H)$^+$
*[10]Solvent for crystallization Experiment 1 [MC$_4$ Receptor Binding Assay]

MC$_4$ receptor binding assay was carried out according to the method described in Pharmacology & Taxicology, 79, 161–165, 1996, HEK-293 cell membranes expressing the human MC$_4$ receptor were purchased from Biolinks Co. The cell membranes were homogenized in a 50 mM Tris hydrochloric acid buffer solution (pH 7.4) containing 2 mM ethylenediamine tetraacetic acid, 10 mM calcium chloride and 100 μM phenylmethanesulfonyl-fluoride. The homogenate was centrifuged at 48,000×g for 20 minutes at 4° C. The precipitate obtained by centrifugation was again homogenized in the same buffer solution, and the homogenate was centrifuged at 48,000×g for 20 minutes at 4° C. This procedure was repeated twice. The precipitate was suspended in 50 mM Tris hydrochloric acid buffer solution (pH 7.4) containing 2 mM ethylenediamine tetraacetic acid, 10 mM calcium chloride, 100 μM phenylmethanesulfonylfluoride and 0.1% bovine serum albumin to adjust to a protein concentration of 100 μg/ml to give a crude membrane preparation which was used for the binding assay. The crude membrane preparation (0.25 ml, 25 μg protein) was reacted with [$^{125}$I]Nle$^4$-D-Phe$^7$-α-MSH (final concentration: 0.2 nM) at 25° C. for 120 minutes. After the completion of the reaction, the reaction solution was filtered under suction on GF/C glass filter presoaked for 2 hours in 50 mM Tris hydrochloric acid buffer solution (pH 7.4) containing 0.5% bovine serum with the use of a cell harvester for receptor binding assay. The radioactivity on the filter paper was measured in a gamma-counter. The binding in the presence of 1 μM Nle$^4$-D-Phe$^7$-α-MSH was defined as non-specific binding. Specific binding was obtained by subtracting the non-specific binding from the total binding, which was the binding in the absence of 1 μM Nle$^4$-D-Phe$^7$-α-MSH. Test compound was dissolved in 100% DMSO, and added simultaneously with [$^{125}$I]Nle$^4$-D-Phe$^7$-α-MSH to the membrane preparation. The IC$_{50}$ value was calculated from the inhibition curve in the concentration range of $10^{-9}$–$10^{-5}$. As a result, for example, Compound 4 showed 164 nM, and optically active Compound 6 showed 90 nM.

Experiment 2

Anxiogenic-like activity inducing action by α-MSH and MTII in Vogel test in rat (Proconflict test) was studied.

α-MSH and MTII were purchased from Peninsula Laboratories. Male SD rats weighing 220 to 240 g (Charles River Japan Inc.) were used for animals. Rats deprived of drinking water for 48 hours were divided into 5 animals for each group. The test compound was administered to rats intracerebroventricularly at 10 µl/2 min. of the test compound which was prepared by dissolving a predetermined amount of α-MSH or MTII in saline containing 0.1% bovine serum albumin. To control rats which were not administered test compound, saline containing 0.1% bovine serum albumin was administered intracerebroventricularly at 10 µl/2 min. Thirty minutes after the administration, rats were placed in a apparatus for the test, and drinking behaviors during the time of free access to drinking water for 3 minutes were measured. During the time of free access to drinking water, an electric shock (0.4 mA) was released, every 2 seconds of cumulative licking time to the drinking nozzle. The evaluation of this experiment was carried out using the number of the electric shocks. Results are shown in FIG. 1.

Symbols # and ## in FIG. 1 show that, when a significant difference test was carried out by Dunnett test, $p<0.05$ and $p<0.01$ represent that there is a significant difference in comparison with the control group treated with saline containing 0.1% bovine serum albumin.

As apparent from the results shown in FIG. 1, the number of times of drinking water was dose-dependently, significantly decreased by the intracerebroventricular administrations of α-MSH and MTII in comparison with the control group.

Experiment 3

Anti-anxiety action of Compound 4 in Table 1 in Vogel test (Conflict test) in rats was studied.

Male SD rats weighing 220 to 240 g (Charles River Japan Inc.) were used. Rats deprived of drinking water for 48 hours were divided into 10 animals for each group. To rats of group to be administered with the test compound was subcutaneously administered the test compound which was prepared by dissolving a predetermined amount of Compound 4 in Table 1 in saline for injection and adding 0.5 M aqueous sodium hydroxide solution to adjust to pH 4–5. Thirty minutes after the administration, rats were placed in a apparatus for the test, and drinking behaviors during the time of free access to drinking water for 3 minutes were measured. During the time of free access to drinking water, an electric shock (1.0 mA) was released, every 2 seconds of cumulative licking time to the drinking nozzle. The evaluation of this experiment was carried out using the number of the electric shocks. Results are shown in FIG. 2.

Symbol ** in FIG. 2 shows that, when a significant difference test was carried out by Dunnett test, $p<0.01$ represents that there is a significant difference in comparison with the control group which were not exposed to an electric shock to drinking nozzle. Symbol ## in FIG. 2 shows that, when a significant difference test was carried out by Dunnett test, $p<0.01$ represents that there is a significant difference in comparison with the group which were treated with an isotonic sodium chloride solution and exposed to electric shocks to drinking nozzle.

As apparent from the results shown in FIG. 2, the number of times of drinking water of the group exposed to an electric shock in comparison with the group which were not exposed to electric shocks. However, this decreased number of times of drinking water was significantly, dose-dependently antagonized by the subcutaneous administration of 1 mg/kg, 3 mg/kg or 10 mg/kg of Compound 4 in Table 1.

Experiment 4

Anti-anxiety action of Compound 4 in Table 1 in forced swim stress-induced anxiety model of rats was studied.

Male SD rats weighing 220 to 240 g (Charles River Japan Inc.) were used. Rats were divided into 10 animals for each group. To rats of group to be administered with the test compound was subcutaneously administered the test compound which was prepared by dissolving a predetermined amount of the test drug in saline for injection and adding 0.5 M aqueous sodium hydroxide solution to adjust to pH 4–5. Thirty minutes after the administration, rats were exposed to a forced swim stress by placing in a black cylinder (20 cm internal diameter, 40 cm high) containing 25 cm deep of water maintained at 25° C. Duration of the forced swim stress was 2 minutes, and the anti-anxiety action was studied by the elevated plus-maze test, which was carried out 5 minutes after the forced swim stress.

The elevated plus-maze used for the test consisted of open arms (10 cm wide, 50 cm long) and close arms (10 cm wide, 50 cm long), and the open arms and the enclosed arms were covered with 1 cm-high and 40 cm-high transparent Plexiglas, respectively. The plus-maze was placed in 50 cm high from the floor. Luminosity at the center of the maze was 40 lux. Each rat was placed in the center of the plus-maze facing one enclosed arm. The amount of time spent in open arms of the maze was recorded during a 5-minute period. Results are shown in Table 3.

Symbol ** in FIG. 3 shows that, when a significant difference test was carried out by Dunnett test, $p<0.01$ represents that there is a significant difference in comparison with the control which is not exposed to the forced swim stress. Symbol ## in FIG. 3 shows that, when a significant difference test was carried out by Dunnett test, $p<0.01$ represents that there is a significant difference in comparison with the group exposed to the forced swim stress by treating with saline.

As apparent from the results shown in FIG. 3, the amount of time spent in open arms of the group exposed to the forced swim stress is significantly decreased in comparison with the group which were not exposed to the forced swim stress. However, this decreased amount of time spent in open arms was significantly, dose-dependently antagonized by the subcutaneous administration of 0.3 mg/kg, 1 mg/kg or 3 mg/kg of Compound 4 in Table 1.

Experiment 5

Anti-depressant action of Compound 4 in Table 1 in olfactory bulbectomized rats was studied.

Male SD rats weighing 220 to 240 g (Charles River Japan Inc.) were used. Rats were anesthetized with sodium pentobarbital, the olfactory bulbs were removed by suction using a metal pipe linked to a water aspirator. Two weeks after the removal of the olfactory bulbs, rats were divided into 10 to 11 animals for each group. The rats of one group were subcutaneously administered once a day for 2 weeks with the test drug which was prepared by dissolving a predetermined amount of the test drug in saline for injection and adding 0.5 M aqueous sodium hydroxide solution to adjust to pH 4–5. Twenty four hours after the final administration, the rats were placed in the center of a circular open field apparatus (70 cm diameter 25 blocks), and the number of crossings among blocks during 3 minutes was counted. Results are shown in FIG. 4.

Symbol ** in FIG. 4 shows that, when a significant difference test was carried out by Dunnett test, p<0.01 represents that there is a significant difference in comparison with the control group of which olfactory bulbs were not removed. Symbol ## in FIG. 4 shows that, when a significant difference test was carried out by Dunnett test, p<0.01 represents that there is a significant difference in comparison of the olfactory bulbectomized group, which were administered with saline.

As apparent from the results shown in FIG. 4, the number of crossings among blocks in the open field of the olfactory bulbectomized rats was significantly increased in comparison with rats whose olfactory bulbs were not removed. However, the increased number of crossings among blocks in the open field was significantly, dose-dependently antagonized by the subcutaneous administration of 1 mg/kg, 3 mg/kg or 10 mg/kg of Compound 4 in Table 1.

From the above results, the compounds, which antagonize $MC_4$ receptor are useful as therapeutic agents of depression or anxiety because of their inhibitory action of anxiogenic-like symptoms and depressive-like symptoms.

Figure 1:
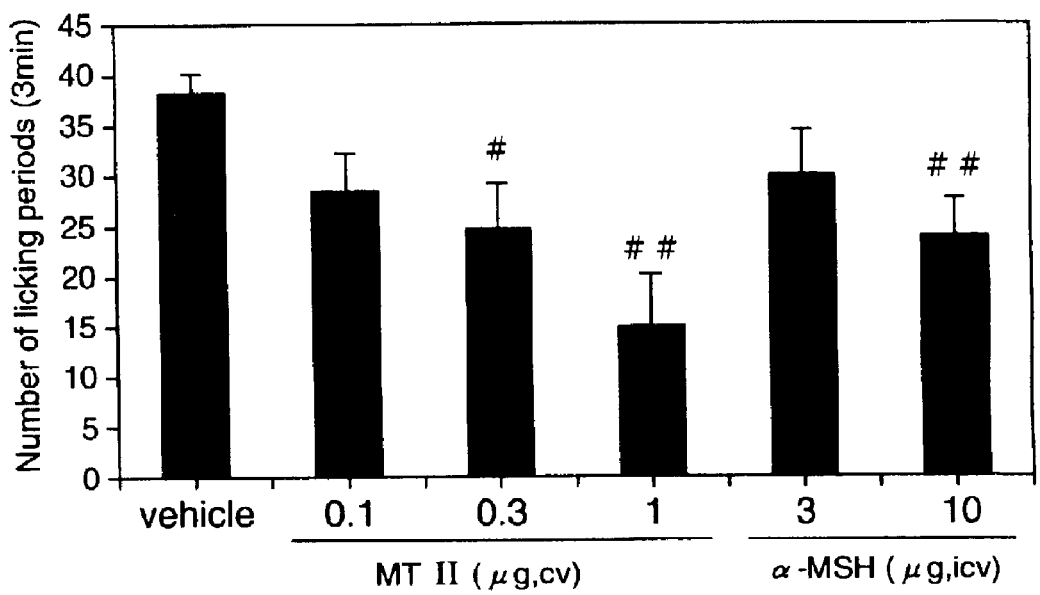
FIG. 1 shows the results of anxiogenic-like activity by Vogel test in rats in Experiment 2.
Figure 2:
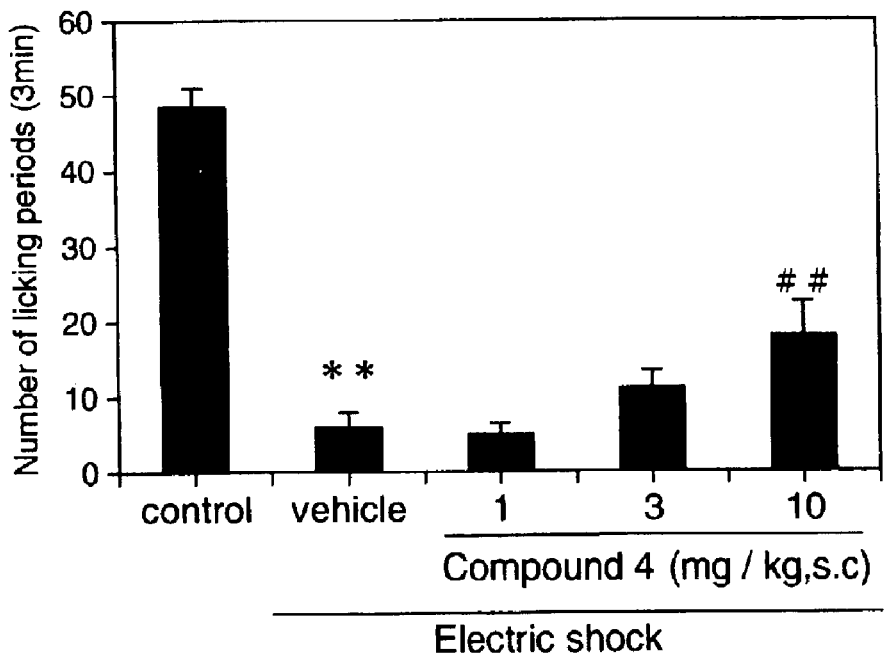
FIG. 2 shows the results of anti-anxiety activity by Vogel test in rats in Experiment 3.
Figure 3:
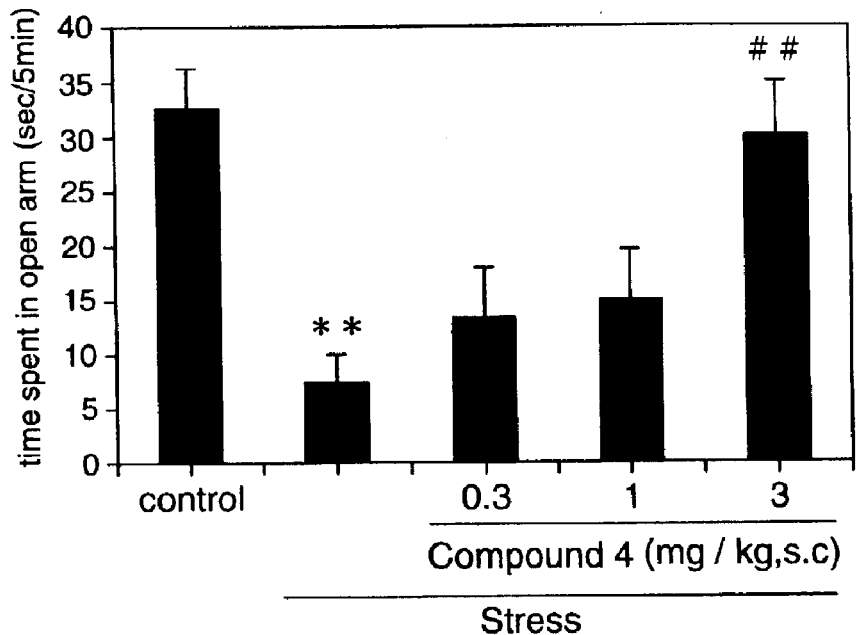
FIG. 3 shows the results of anti-anxiety activity in forced swim stress-induced anxiety model rats in Experiment 4.
Figure 4:
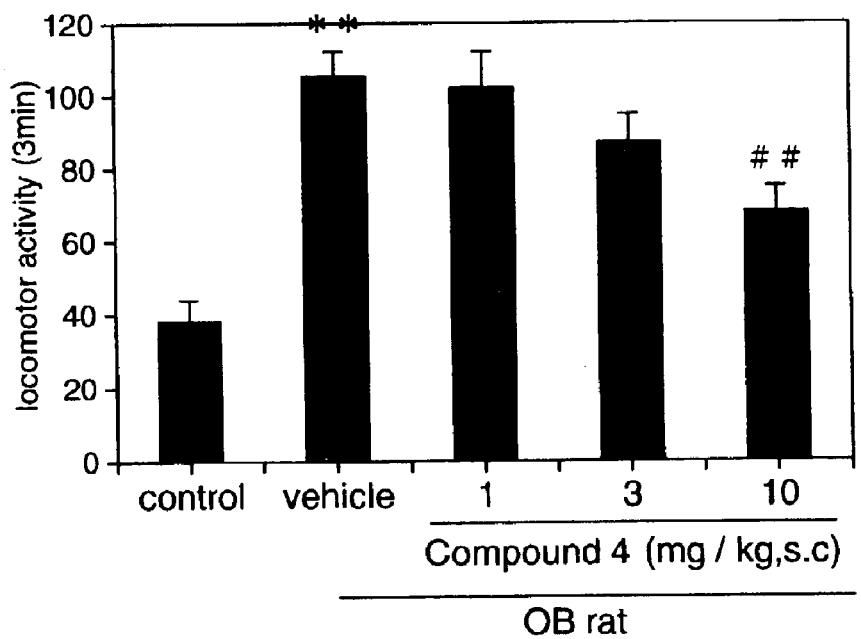
FIG. 4 shows the results of anti-depression activity in olfactory bulbectomized rats in Experiment 5.

What is claimed is:

1. The therapeutic preparation for anxiety neurosis or depression which contains a piperazine derivative having $MC_4$ receptor antagonist action as an effective ingredient, wherein the piperazine derivative is represented by Formula 1:

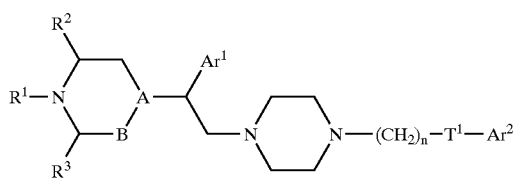

wherein $Ar^1$ is a phenyl group, a substituted phenyl group, a naphthyl group or a substituted naphthyl group; $Ar^2$ is a naphthyl group, a substituted naphthyl group, a quinolyl group, a group represented by the formula:

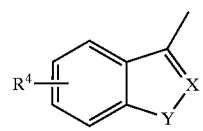

(wherein $R^4$ is a hydrogen atom or a halogen atom; and X—Y is CH—NH, CH—O, CH—S or N—O) or a group represented by the formula:

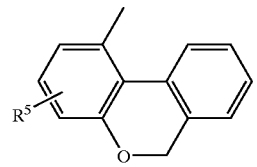

(wherein $R^5$ is a hydrogen atom, a hydroxyl group or a $C_{1-10}$ alkoxy group); $R^1$ is a hydrogen atom, a $C_{1-10}$ alkyl group, a $C_{3-8}$ cycloalkyl group, a $C_{3-10}$ alkenyl group, a phenyl group, a 1-cyanoethyl group, or a pyrimidin-2-yl group; $R^2$ and $R^3$ are the same or different, and are each a hydrogen atom or a $C_{1-10}$ alkyl group; A-B is N—$CH_2$, CH—$CH_2$, C(OH)—$CH_2$ or C=CH; $T^1$ is a single bond, —N($R^{60}$)— (wherein $R^6$ is a hydrogen atom or a $C_{1-10}$ alkyl group), —O—, —CH=CH— or —C(=O)—; n is an integer of from 1 to 10 when $T^1$ is single bond, —CH=CH— or —C(=O)—, and n is an integer of from 2 to 10 when $T^1$ is —N($R^8$)— or —O—], or a pharmaceutically acceptable salt thereof.

2. The therapeutic preparation for anxiety neurosis or depression according to claim 1 wherein, in Formula 1, $Ar^1$ is a phenyl group or a substituted phenyl group; and $Ar^2$ is a naphthyl group or a substituted naphthyl group.

3. The therapeutic preparation for anxiety neurosis or depression according to claim 1 wherein, in Formula 1, $Ar^1$ is a phenyl group or a substituted phenyl group; $Ar^2$ is a naphthyl group or a substituted naphthyl group; $R^1$ is a hydrogen atom, a $C_{1-10}$ alkyl group or a $C_{3-8}$ cycloalkyl group; $R^2$ and $R^3$ are each a hydrogen atom; A-B is N—$CH_2$ or CH—$CH_2$, and $T^1$ is a single bond.

4. The therapeutic preparation for anxiety neurosis or depression according to claim 1 wherein the substituted phenyl group is a phenyl group substituted with 1 to 3 substituents independently selected from the group consisting of a $C_{1-10}$ alkyl group, a $C_{1-10}$ alkoxy group, a benzyloxy group, a hydroxyl group, a halogen atom, a nitro group an amino group, an amino group substituted with one or two $C_{1-6}$ alkyl groups, a trifluoromethyl group, a cyano group, a carbamoyl group and a phenyl group; and a substituted naphthyl group is a naphthyl group substituted with 1 to 3 substituents independently selected from the group consisting of a $C_{1-10}$ alkyl group, a $C_{1-10}$ alkoxy group, a hydroxyl group, a $C_{1-5}$ alkoxycarbonylmethoxy group, a carbamoylmethoxy group, a halogen atom, an amino group and an amino group substituted with one or two $C_{1-6}$ alkyl group.

5. The therapeutic preparation for anxiety neurosis or depression according to claim 1 wherein, in Formula 1, $Ar^1$ is a phenyl group or a substituted phenyl group; $Ar^2$ is a group of the formula:

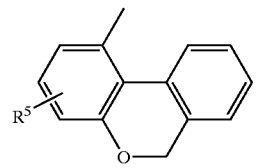

(wherein $R^5$ is a hydrogen atom, a hydroxyl group or a $C_{1-10}$ alkoxy group); $R^1$ is a hydrogen atom, a $C_{1-10}$ alkyl group or a $C_{3-8}$ cycloalkyl group; $R^2$ and $R^3$ are each a hydrogen atom; A-B is N—CH$_2$ or CH—CH$_2$; and T$^1$ is a single bond.

6. The therapeutic preparation for anxiety neurosis or depression according to claim 5 wherein the substituted phenyl group is a phenyl group substituted with 1 to 3 substituents independently selected from the group consisting of a C$_{1-10}$ alkyl group, a C$_{1-10}$ alkoxy group, a benzyloxy group, a hydroxyl group, a halogen atom, a nitro group, an amino group, an amino group substituted with one or two C$_{1-6}$ alkyl groups, a trifluoromethyl group, a cyano group, a carbamoyl group and a phenyl group.

7. A piperazine derivative represented by Formula 1:

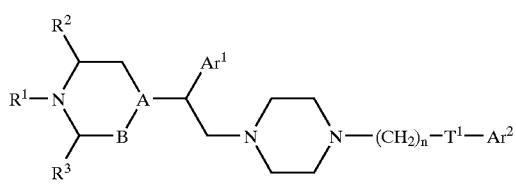

1

┼wherein Ar$^1$ is a phenyl group, a substituted phenyl group, a naphthyl group or a substituted naphthyl group; Ar$^2$ is a naphthyl group, a substituted naphthyl group, a quinolyl group, a group represented by the formula:

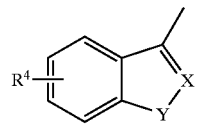

(wherein R$^4$ is a hydrogen atom or a halogen atom; and X—Y is CH—NH, CH—O, CH—S or N—O) or a group represented by the formula:

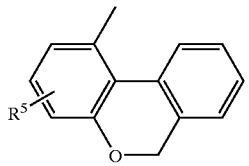

(wherein R$^5$ is a hydrogen atom, a hydroxyl group or a C$_{1-10}$ alkoxy group); R$^1$ is a hydrogen atom, a C$_{1-10}$ alkyl group, a C$_{3-8}$ cycloalkyl group, a C$_{3-10}$ alkenyl group, a phenyl group, a 1-cyanoethyl group, or a pyrimidin-2-yl group; R$^2$ and R$^3$ are the same or different, and are each a hydrogen atom or a C$_{1-10}$ alkyl group; A-B is N—CH$_2$, CH—CH$_2$, C(OH)—CH$_2$ or C═CH; T$^1$ is a single bond, —N(R$^6$)— (wherein R$^6$ is a hydrogen atom or a C$_{1-10}$ alkyl group), —O—, —CH═CH— or —C(═O)—; n is an integer of from 1 to 10 when T$^1$ is a single bond, —CH═CH— or —C(═O)—, and n is an integer of from 2 to 10 when T$^1$ is —N(R$^6$)— or —O—┼, or a pharmaceutically acceptable salt thereof.

8. The piperazine derivative of Formula 1 or a pharmaceutically acceptable salt thereof according to claim 7 wherein Ar$^1$ is a phenyl group or a substituted phenyl group; and Ar$^2$ is a naphthyl group or a substituted naphthyl group.

9. The piperazine derivative of Formula 1 or a pharmaceutically acceptable salt thereof according to claim 7 wherein Ar$^1$ is a phenyl group or a substituted phenyl group; Ar$^2$ is a naphthyl group or a substituted naphthyl group; R$^1$ is a hydrogen atom, a C$_{1-10}$ alkyl group or a C$_{3-8}$ cycloalkyl group; R$^2$ and R$^3$ are each a hydrogen atom; A-B is N—CH$_2$ or CH—CH$_2$; and T$^1$ is a single bond.

10. The piperazine derivative of Formula 1 or a pharmaceutically acceptable salt thereof according to claim 7 wherein the substituted phenyl group is a phenyl group substituted with 1 to 3 substituents independently selected from the group consisting of a C$_{1-10}$ alkyl group, a C$_{1-10}$ alkoxy group, a benzyloxy group, a hydroxyl group, a halogen atom, a nitro group, an amino group, an amino group substituted with one or two C$_{1-6}$ alkyl groups, a trifluoromethyl group, a cyano group, a carbamoyl group and a phenyl group, and a substituted naphthyl group is a naphthyl group substituted with 1 to 3 substituents independently selected from the group consisting of a C$_{1-10}$ alkyl group, a C$_{1-10}$ alkoxy group, a hydroxyl group, a C$_{1-5}$ alkoxycarbonylmethoxy group, a carbamoylmethoxy group, a halogen atom, an amino group and an amino group substituted with one or two C$_{1-6}$ alkyl groups.

11. The piperazine derivative of Formula 1 or a pharmaceutically acceptable salt thereof according to claim 7 wherein Ar$^1$ is a phenyl group or a substituted phenyl group; Ar$^2$ is a group of the formula:

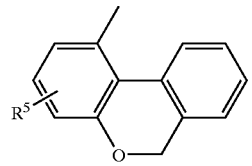

(wherein R$^5$ is a hydrogen atom, a hydroxyl group or a C$_{1-10}$ alkoxy group); R$^1$ is a hydrogen atom, a C$_{1-10}$ alkyl group or a C$_{3-8}$ cycloalkyl group; R$^2$ and R$^3$ are each a hydrogen atom; A-B is N—CH$_2$ or CH—CH$_2$; and T$^1$ is a single bond.

12. The piperazine derivative or a pharmaceutically acceptable salt thereof according to claim 11 wherein the substituted phenyl group is a phenyl group substituted with 1 to 3 substituents independently selected from the group consisting of a C$_{1-10}$ alkyl group, a C$_{1-10}$ alkoxy group, a benzyloxy group, a hydroxyl group, a halogen atom, a nitro group, an amino group, an amino group substituted with one or two C$_{1-6}$ alkyl groups, a trifluoromethyl group, a cyano group, a carbamoyl group and a phenyl group.

* * * * *

UNITED STATES PATENT AND TRADEMARK OFFICE
CERTIFICATE OF CORRECTION

PATENT NO. : 6,949,552 B2
APPLICATION NO. : 10/311429
DATED : September 27, 2005
INVENTOR(S) : Nakazato et al.

Page 1 of 1

It is certified that error appears in the above-identified patent and that said Letters Patent is hereby corrected as shown below:

Column 43,
Line 53, "}wherein" should read -- wherein --.

Column 44,
Line 16, "-N($R^{60}$)-" should read -- -N($R^6$)- --.
Line 21, "-N($R^8$)-" should read -- -N($R^6$)- --; and "—O—}" should read -- —O— --.
Line 50, "group" should read -- groups --.

Column 45,
Line 23, "}wherein" should read -- wherein --.
Line 60, "—O—}" should read -- —O— --.

Signed and Sealed this

Twenty-seventh Day of June, 2006

JON W. DUDAS
*Director of the United States Patent and Trademark Office*